US006197548B1

(12) United States Patent
Clare et al.

(10) Patent No.: US 6,197,548 B1
(45) Date of Patent: Mar. 6, 2001

(54) TRANSFORMED PICHIA EXPRESSING THE PERTACTIN ANTIGEN

(75) Inventors: Jeffrey John Clare; Michael Anthony Romanos, both of Beckenham (GB)

(73) Assignee: Medeva Pharma Limited (GB)

( * ) Notice: Subject to any disclaimer, the term of this patent is extended or adjusted under 35 U.S.C. 154(b) by 0 days.

(21) Appl. No.: 08/460,269

(22) Filed: Jun. 2, 1995

Related U.S. Application Data

(62) Continuation of application No. 08/305,792, filed on Sep. 13, 1994, now abandoned, which is a continuation of application No. 07/937,822, filed as application No. PCT/GB91/00487 on Mar. 28, 1991, now abandoned.

(30) Foreign Application Priority Data

Apr. 2, 1990 (GB) .................................................. 9007416
Mar. 28, 1991 (WO) .................................. PCT/GB91/00487

(51) Int. Cl.[7] ........................... C12N 15/09; C12N 1/19
(52) U.S. Cl. ................................... 435/69.3; 435/254.23
(58) Field of Search ........................... 435/254.23, 69.1, 435/69.3; 424/190.1, 254.1, 253.1

(56) References Cited

U.S. PATENT DOCUMENTS

| | | |
|---|---|---|
| 4,837,148 | 6/1989 | Cregg . |
| 4,879,213 | 11/1989 | Fox et al. . |
| 4,895,800 | 1/1990 | Tschopp et al. . |
| 4,929,555 | 5/1990 | Cregg et al. . |
| 4,997,915 | 3/1991 | Tan et al. . |
| 5,085,862 | 2/1992 | Klein et al. . |
| 5,221,618 | 6/1993 | Klein et al. . |
| 5,237,052 | 8/1993 | Novotny . |
| 5,244,657 | 9/1993 | Klein et al. . |
| 5,276,142 | 1/1994 | Gotto . |
| 5,324,639 | 6/1994 | Brierley et al. . |
| 5,332,583 | 7/1994 | Klein et al. . |
| 5,358,868 | 10/1994 | Klein et al. . |
| 5,389,540 | 2/1995 | Makoff et al. . |
| 5,433,945 | 7/1995 | Klein et al. . |
| 5,438,120 | 8/1995 | Novotny et al. . |
| 5,439,810 | 8/1995 | Loosmore et al. . |
| 5,444,159 | 8/1995 | Jackson et al. . |
| 5,571,694 | 11/1996 | Makoff et al. . |
| 5,648,080 | 7/1997 | Novotny et al. . |
| 5,667,787 | 9/1997 | Jackson et al. . |

FOREIGN PATENT DOCUMENTS

| | | |
|---|---|---|
| 0162639 | 11/1985 | (EP) . |
| 0180899 | 5/1986 | (EP) . |
| 0226846 | 7/1987 | (EP) . |
| 0248227 | 12/1987 | (EP) . |
| 0263311 | 4/1988 | (EP) . |
| 0 336 736 A1 | 10/1989 | (EP) . |
| 0341746 | 11/1989 | (EP) . |
| 339567 * | 11/1989 | (EP) . |
| 0339568 | 11/1989 | (EP) . |
| 0 527 725 B1 | 2/1993 | (EP) . |
| WO 91/15571 | 10/1991 | (WO) . |
| WO 93/21950 | 11/1993 | (WO) . |

OTHER PUBLICATIONS

Airaksinen et al., "Expression of the Outer Membrane Protein P.69 of *Bordetella pertussis* in *Bacillus subtilis*," *Biotech. Letters*, 13(5):305–310 (1991).

Betsou et al., "Cloning and Sequence of the *Bordetella bronchiseptica* Adenylate Cyclase–Hemolysin–Encoding Gene: Comparison with the *Bordetella pertussis* Gene," *Gene*, 162:165–166 (1995).

Betsou et al., "The C–Terminal Domain is Essential for Protective Activity of the *Bordetella pertussis* Adenylate Cyclase–Hemolysin," *Infection and Immunity*, 63(9):3309–3315 (1995).

Brennan et al., "Identification of a 69–Kilodalton Nonfimbrial Protein as an Agglutinogen of *Bordetella pertussis*," *Infection and Immunity*, 56(12):3189–3195 (1988).

Brennan et al., "Structural and Functional Properties of a 69–Kilodalton Outer Membrane Protein of *Bordetella pertussis*," *Tokai J. Exp. Clin. Med.*, 13(Suppl.):211–215 (1988).

Charles et al., "Expression of P.69/Pertactin from *Bordetella pertussis* in a Baculovirus/Insect Cell Expression System: Protective Properties of the Recombinant Protein," *Res. Microbiol.*, 144:681–690 (1993).

Charles et al., "Identification and Characterization of a Protective Immunodominant B Cell Epitope of Pertactin (P69) from *Bordetella pertussis*," *Eur. J. Immunol.*, 21:1147–1153 (1991).

Charles et al., "Molecular Cloning and Analysis of P.69, a vir–Controlled Protein from, *Bordetella pertussis*," *Tokai. J. Exp. Clin. Med.*, 13(Suppl.):227–234 (1988).

Clare et al., "High–Level Expression of Tetanus Toxin Fragment C in *Pichia pastoris* Strains Containing Multiple Tandem Integrations of the Gene," *Bio/Technology*, 9:455–460 (1991).

Confer et al., "Phagocyte Impotence Caused by an Invasive Bacterial Adenylate Cycalse," *Science*, 217:948–950 (1982).

Cregg et al., "*Pichia pastoris* as a Host System for Transformations," *Mol. and Cell. Biol.*, 5(12):3376–3385 (1985).

Cregg et al., "Recent Advances in the Expression of Foreign Genes in *Pichia pastoris*," *Biotechnology*, 11(8):905–910 (1993).

(List continued on next page.)

*Primary Examiner*—Marianne P. Allen
(74) *Attorney, Agent, or Firm*—Millen, White, Zelano, & Branigan, P.C.

(57) ABSTRACT

Production of Bordetella pertactin antigens by expression in the methyltrophic yeast, Pichia; expression vectors containing DNA encoding the antigens and Pichia transformants containing the one of more copies of the DNA encoding a pertactin antigen.

17 Claims, 19 Drawing Sheets

OTHER PUBLICATIONS

Figure 2A:
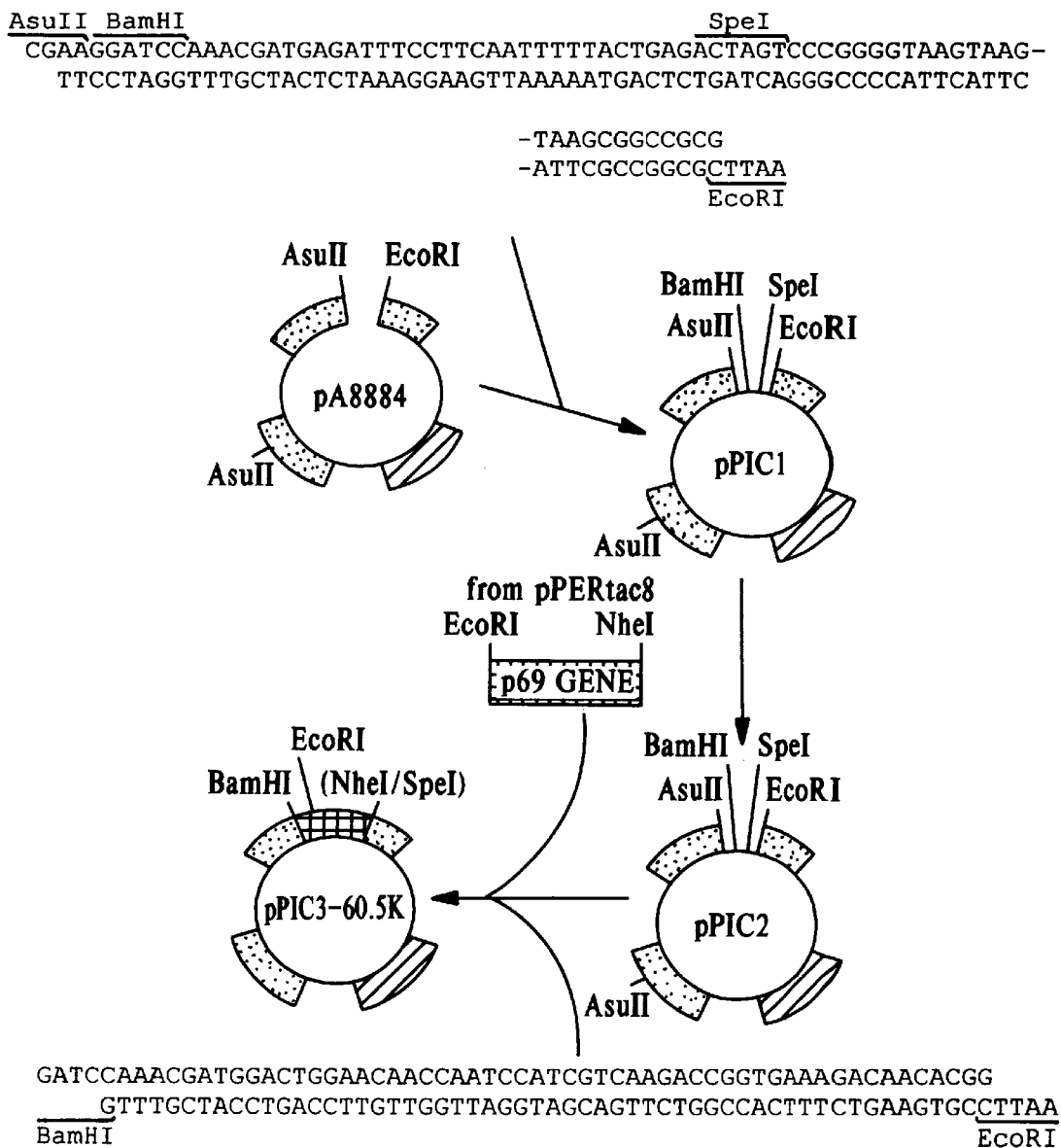

Cronin et al., "Prokaryotic Adenylate Cyclase Toxin Stimulates Anterior Pituitary Cells in Culture," *Amer. Journ. Physiol.*, 251(2):E164–171 (1986).

DeMagistris et al., "Dissecting Human T Cell Responses Against Bordetella Species," *Journ. Exp. Med.*, 168:1351–1362 (1988).

Despreaux et al., *Gene*, 131:35–41 (1993).

Englard et al., "Precipitation Techniques," *Meth. Enzym.*, 182:285–300 (1990).

Gould–Kostka et al., "Purification and Analysis of the Antigenicity of a 69,000 Da Protein from *Bordetella pertussis*," *FEMS Microbiol. Letters*, 67:285–290 (1990).

Greco et al., "A Controlled Trial of Two Acellular Vaccines and One Whole–Cell Vaccine Against Pertussis," *New Eng. J. Med.*, 334(6):341–348 (1996).

Guiso et al., "*Bordetella pertussis* Adenylate Cyclase: A Protective Antigen Against Lethality and Bacterial Colonization in Murine Respiratory and Intracerebral Models," Proceedings of the Sixth International Symposium on Pertussis, NIH, Bethesda, Maryland, USA, Sep. 26–28, 1990, pp. 207–211 (1990).

Gustafsson et al., "A Controlled Trial of a Two–Component Acellular, a Five–Component Acellular, and a Whole–Cell Pertussis Vaccine," *New Eng. J. Med.*, 334(6):349–355 (1996).

Hallewell et al., *Biotechnology*, 5:363–366 (1987).

Hedenskog et al., "A Clinical Trial of a Monocomponent Pertussis Toxoid Vaccine," *Amer. Journ. Dis. Child.*, 141(8):844–847 (1987).

Hewlett et al., Pathogenesis and Immunity in Pertussis (Eds. Wardlaw and Parton), pp. 193–209 (1988).

Kallings et al., "Placebo–Controlled Trial of Two Acellular Pertussis Vaccines in Sweden—Protective Efficacy and Adverse Events," *The Lancet*, Apr. 30, 1988, pp. 955–960 (1988).

Kniskern et al., *Gene*, 46:135–141 (1986).

Ladant et al., "*Bordetella pertussis* Adenylate Cyclase, Purification, Characterization, and Radioimmunoassay," *Journ. Biol. Chem.*, 261(34):16264–16269 (1986).

Linn, S., "Strategies and Considerations for Protein Purifications," *Meth. Enzym.*, 182:9–15 (1990).

Manclark et al., *Developments in Biological Standardization*, 61:27–41 (1985).

Mangold et al., "Secretion and Antigenicity of Hepatitis B Virus Small Envelope Proteins Lacking Cysteines in the Major Antigenic Region," *Virology*, 211:535–543 (1995).

Monneron et al., "Immunological Relatedness Between *Bordetella pertussis* and Rat Brain Adenylyl Cyclases," *Biochemistry*, 27:536–539 (1988).

Montaraz et al., "Identification of a 68–Kilodalton Protective Protein Antigen from *Bordetella bronchiseptica*," *Infection and Immunity*, 47(3):744–751 (1985).

Moss et al., "Cyclic Nucleotides: Mediators of Bacterial Toxin Action in Disease," *Ann. Int. Med.*, 101(5):653–666 (1984).

Novotny et al., "Bordetella Adenylate Cyclase: A Genus Specific Protective Antigen and Virulence Factor," *Develop. Biol. Stand.*, 61:27–41 (1985).

Novotny et al., "Adenylate Cyclase Activity of a 68,000–Molecular–Weight Protein Isolated from the Outer Membrane of *Bordetella bronchiseptica*," *Infection and Immunity*, 50(1):199–206 (1985).

Pohl, T., "Concentration of Proteins and Removal of Solutes," *Meth. Enzym.*, 182:68–83 (1990).

Relman et al., "Filamentous Hemagglutinin of *Bordetella pertussis*: Nucleotide Sequence and Crucial Role in Adherence," *Proc. Natl. Acad. Sci. USA*, 86:2637–2641 (1989).

Romanos et al., "Foreign Gene Expression in Yeast: A Review," *Yeast*, 8:423–488 (1992).

Romanos et al., "Recombinant *Bordetella pertussis* Pertactin (P69) From the Yeast *Pichia pastoris*: High–Level Production and Immunological Properties," *Vaccine*, 9:901–906 (1991).

Romanos et al., "Expression of Tetanus Toxin Fragment C in Saccharomyces: Complete Gene Synthesis is Required to Eliminate Multiple Transcriptional Terminators," 15$^{th}$ International Conference on Yeast Genetics and Molecular Biology, *Yeast*, 6(special issue):S427 (1990).

Rossomando, E., "Ion–Exchange Chromatography," *Meth. Enzym.*, 182:309–317 (1990).

Sato et al., "Development of a Pertussis Component Vaccine in Japan," *The Lancet*, Jan. 21, 1984, pp. 122–126 (1984).

Scorer et al., *Biotechnology*, 12:181–184 (1994).

Shahin et al., "Characterization of the Protective Capacity and Immunogenicity of the 69–kD Outer Membrane Protein of *Bordetella Pertussis*," *Journ. Exp. Med.*, 171:63–73 (1990).

Sreekrishna et al., *J. Basic Microbiol.*, 28(4):265–278 (1988).

Sreekrishna et al., *Industrial Microorganisms Basic and Applied Molecular Genetics*, Chapter 16, pp. 119–126 (1993).

Sreekrishna et al., "Invertase Gene (SUC2) of *Saccharomyces cerevisiae* as a Dominant Marker for Transformation of *Pichia pastoris*," *Gene*, 59:115–125 (1987).

Stellwagon, E., "Gel Filtration," *Meth. Enzym.*, 182:317–328 (1990).

Storsaeter et al., "Secondary Analyses of the Efficacy of Two–Acellular Pertussis Vaccines Evaluated in a Swedish Phase III Trial," *Vaccine*, 8(1):457–461 (1990).

Tamura et al., "Effects of Pertussis Toxin on Delayed–Type Hypersensitivity Responses and on the Activity of Suppressor T Cells on the Responses," *Cell. Immun.*, 81:219–228 (1983).

Thomas et al., "Human Serum Antibody Responses to *Bordetella pertussis* Infection and Pertussis Vaccination," *Journ. Infect. Dis.*, 159(2):211–218 (1989).

Tschopp et al., "Expression of the lacZ Gene from Two Methanol–Regulated Promoters in *Pichia pastoris*," *Nucl. Acids. Res.*, 15(9):3859–3876 (1987).

Weiss et al., Tn–5 Induced Mutations Affecting Virulence Factors of *Bordetella pertussis*, *Infection and Immunity*, 42(1):33–41 (1983).

Westcott et al., Resolution of Adenylate Cyclase Sensitive and Insensitive to $Ca^{2+}$ and Calcium–dependent Regulatory Protein (CDR) by CDB–Sepharose Affinity Chromatography, *Proc. Natl. Acad. Sci. USA*, 76(1):204–208 (1979).

Wolff et al., "Activation of *Bordetella pertussis* Adenylate Cyclase by the Carboxyl–Terminal Tryptic Fragment of Calmodulin," *Biochemistry*, 25:7950–7955 (1986).

Lazar et al. Molecular and Cellular Biology 8(3):1247–1252, Mar. 1988.

Burgess et al. Journal of Cell Biology 111:2129–2138, Nov. 1990.

"Molecular Cloning and Characterization of Protective Outer Membrane Protein" I.G. Charles et al, Proc. Natl. Acad. Sci., 1989, pp. 3554–3558.

"High–Level Expression and Efficient Assembly of Hepatitis B Surface Antigen in the Methylotrophic Yeast", Biotechnology, 5 (1987) May, No. 5, pp. 479–485.

M.A. Romanos et al, Yeast, vol. 6, Special Issue, 5428, 1990, 15th International Conference on Yeast Genetics and Molecular Biology.

Report on Two Fatal Cases, Parapertussis Pneumonia, W. Zuelzer, M.D. et al p. 498 and pp. 494–497, The Journal of Pediatrics.

Am. Journal of Veterinary Research, Turbinate Atrophy in Young Pigs Exposed to *Brodetella Bronchiseptica, Pasteurella Multocida*, and Combined Inoculum, D.L. Harris et al, pp. 777–784.

Heterologous Gene Expression in *Saccharomyces Cerevisiae*, S.M. Kingsman et al Biotechnology & Genet. Engin. Reviews, vol. 3, pp. 377–416, 1985.

Expression of Polyoma Virus Middle–T Antigen in *Saccharomyces Cerevisiae*, Belsham et al, Eur. J. Biochem. 156, pp. 413–421, 1986.

Synthesis of *Escherichia Coli* Outer Membrane OmpA Protein in Yeasts, Janowitz et al, Gene 20, pp. 347–358, 1982.

Influenza Viral (A/WSN/33) Hemagglutinin is Expressed and Glycosyslated in the Yeast *Saccharomyces Cerevisiae*, Jabbar et al. Proc. Natl. Acad. Sci. USA 82, pp. 2019–2023.

Protective Surface Antigen P69 of *Bordetella Pertussis:* Its Characterization and Very High Level Expression in *Escherichia Coli*, Makoff et al (1990) p. 1030.

High–Level Expression, Purification and Characterization of Recombinant Human Tumor Necrosis Factor Synthesized in the Methylotrophic Yeast *Pichia Pastoris*, K. Sreekrishna et al, Biochemistry, 1989, 28, pp. 4117–4125.

Clonal Variation in the Expression of Human Tumor Necrosis Factor (NF) In the Methylotrophic Yeast *Pichia Pastoris* Sreekrishna et al.

Notice of Statement of Opposition to EP 0 527 752.*

M.E. Digan et al., *Dev. in Industrial Microbiology, vol. 29, Suppl. 3)*, pp. 59–65 (1988).*

Airaksinen et al., "Expression of the Outer Membrane Protein P.69 of *Bordetella pertussis*, in *Bacillus subtilis*, ", *Biotech. Letters*, 13(5):305–310 (1991).

Betsou et al., "Cloning and Sequence of the *Bordetella bronchiseptica*, Adenylate Cyclase–Hemolysin–Encoding Gene: Comparison with the *Bordetella pertussis*, gene, ", *Gene*, 162:165–166 (1995).

* cited by examiner

| | |
|---|---|
| ATCGATGATA CGTCGCTGTA ACACGACAAA TAGCGTGCGT TGCAGCGGTT CTGGATGGCG | 60 |
| TTATTCGTAC TTTTGCTGCG CCCATTCTTC CCTGTTCCAT CGCGGTGCGG GCATGGCGGG | 120 |

```
CGTCTGCTCT CCACCTGGCA TCCA ATG AAC ATG TCT CTG TCA CGC ATT GTC    171
                          Met Asn Met Ser Leu Ser Arg Ile Val
                           1               5

AAG GCG GCG CCC CTG CGC CGC ACC ACG CTG GCC ATG GCG CTG GGC GCG   219
Lys Ala Ala Pro Leu Arg Arg Thr Thr Leu Ala Met Ala Leu Gly Ala
 10              15                  20                  25

CTG GGC GCC GCC CCG GCG GCG CAT GCC GAC TGG AAC AAC CAG TCC ATC   267
Leu Gly Ala Ala Pro Ala Ala His Ala Asp Trp Asn Asn Gln Ser Ile
             30                  35                  40

GTC AAG ACC GGT GAG CGC CAG CAT GGC ATC CAT ATC CAG GGC TCC GAC   315
Val Lys Thr Gly Glu Arg Gln His Gly Ile His Ile Gln Gly Ser Asp
             45                  50                  55

CCG GGC GGC GTA CGG ACC GCC AGC GGA ACC ACC ATC AAG GTA AGC GGC   363
Pro Gly Gly Val Arg Thr Ala Ser Gly Thr Thr Ile Lys Val Ser Gly
         60                  65                  70

CGT CAG GCC CAG GGC ATC CTG CTA GAA AAT CCC GCG GCC GAG CTG CAG   411
Arg Gln Ala Gln Gly Ile Leu Leu Glu Asn Pro Ala Ala Glu Leu Gln
     75                  80                  85

TTC CGG AAC GGC AGT GTC ACG TCG TCG GGA CAG TTG TCC GAC GAT GGC   459
Phe Arg Asn Gly Ser Val Thr Ser Ser Gly Gln Leu Ser Asp Asp Gly
 90                  95                 100                 105

ATC CGG CGC TTT CTG GGC ACC GTC ACC GTC AAG GCC GGC AAG CTG GTC   507
Ile Arg Arg Phe Leu Gly Thr Val Thr Val Lys Ala Gly Lys Leu Val
                 110                 115                 120

GCC GAT CAC GCC ACG CTG GCC AAC GTT GGC GAC ACC TGG GAC GAC GAC   555
Ala Asp His Ala Thr Leu Ala Asn Val Gly Asp Thr Trp Asp Asp Asp
             125                 130                 135

GGC ATC GCG CTC TAT GTG GCC GGC GAA CAG GCC CAG GCC AGC ATC GCC   603
Gly Ile Ala Leu Tyr Val Ala Gly Glu Gln Ala Gln Ala Ser Ile Ala
             140                 145                 150

GAC AGC ACC CTG CAG GGC GCT GGC GGC GTG CAG ATC GAG CGC GGC GCC   651
Asp Ser Thr Leu Gln Gly Ala Gly Gly Val Gln Ile Glu Arg Gly Ala
         155                 160                 165

AAT GTC ACG GTC CAA CGC AGC GCC ATC GTC GAC GGG GGC TTG CAT ATC   699
Asn Val Thr Val Gln Arg Ser Ala Ile Val Asp Gly Gly Leu His Ile
170                 175                 180                 185

GGC GCC CTG CAG TCA TTG CAG CCG GAA GAC CTT CCG CCC AGC CGG GTG   747
Gly Ala Leu Gln Ser Leu Gln Pro Glu Asp Leu Pro Pro Ser Arg Val
                 190                 195                 200
```

Fig. 1A-1

```
GTG CTG CGC GAC ACC AAC GTG ACC GCC GTG CCC GCC AGC GGC GCG CCC    795
Val Leu Arg Asp Thr Asn Val Thr Ala Val Pro Ala Ser Gly Ala Pro
            205             210             215

GCG GCG GTG TCT GTG TTG GGG GCC AGT GAG CTT ACG CTC GAC GGC GGG    843
Ala Ala Val Ser Val Leu Gly Ala Ser Glu Leu Thr Leu Asp Gly Gly
            220             225             230

CAC ATC ACC GGC GGG CGG GCA GCG GGG GTG GCG GCC ATG CAA GGG GCG    891
His Ile Thr Gly Gly Arg Ala Ala Gly Val Ala Ala Met Gln Gly Ala
            235             240             245

GTC GTG CAT CTG CAG CGC GCG ACG ATA CGG CGC GGG GAC GCG CTT GCC    939
Val Val His Leu Gln Arg Ala Thr Ile Arg Arg Gly Asp Ala Leu Ala
250             255             260             265

GGC GGT GCG GTT CCC GGC GGT GCG GTT CCC GGT GGT GCG GTT CCC GGC    987
Gly Gly Ala Val Pro Gly Gly Ala Val Pro Gly Gly Ala Val Pro Gly
            270             275             280

GGC TTC GGT CCC GGC GGC TTC GGT CCC GTC CTC GAC GGC TGG TAT GGC   1035
Gly Phe Gly Pro Gly Gly Phe Gly Pro Val Leu Asp Gly Trp Tyr Gly
            285             290             295

GTG GAC GTA TCG GGC TCC AGC GTG GAG CTG GCC CAG TCG ATC GTC GAG   1083
Val Asp Val Ser Gly Ser Ser Val Glu Leu Ala Gln Ser Ile Val Glu
            300             305             310

GCG CCG GAG CTG GGC GCC GCA ATC CGG GTG GGC CGC GGC GCC AGG GTG   1131
Ala Pro Glu Leu Gly Ala Ala Ile Arg Val Gly Arg Gly Ala Arg Val
            315             320             325

ACG GTG CCG GGC GGC AGC TTG TCC GCA CCG CAC GGC AAT GTC ATC GAG   1179
Thr Val Pro Gly Gly Ser Leu Ser Ala Pro His Gly Asn Val Ile Glu
330             335             340             345

ACC GGC GGC GCG CGT CGC TTT GCG CCT CAA GCC GCG CCC CTG TCG ATC   1227
Thr Gly Gly Ala Arg Arg Phe Ala Pro Gln Ala Ala Pro Leu Ser Ile
            350             355             360

ACC TTG CAG GCC GGC GCG CAT GCC CAG GGG AAA GCG CTG CTG TAC CGG   1275
Thr Leu Gln Ala Gly Ala His Ala Gln Gly Lys Ala Leu Leu Tyr Arg
            365             370             375

GTC CTG CCG GAG CCC GTG AAG CTG ACG CTG ACC GGG GGC GCC GAT GCG   1323
Val Leu Pro Glu Pro Val Lys Leu Thr Leu Thr Gly Gly Ala Asp Ala
            380             385             390

CAG GGC GAC ATC GTC GCG ACG GAG CTG CCC TCC ATT CCC GGC ACG TCG   1371
Gln Gly Asp Ile Val Ala Thr Glu Leu Pro Ser Ile Pro Gly Thr Ser
            395             400             405

ATC GGG CCG CTC GAC GTG GCG CTG GCC AGC CAG GCC CGA TGG ACG GGC   1419
Ile Gly Pro Leu Asp Val Ala Leu Ala Ser Gln Ala Arg Trp Thr Gly
410             415             420             425
```

Fig. 1A-2

```
GCT ACC CGC GCG GTC GAC TCG CTG TCC ATC GAC AAC GCC ACC TGG GTC        1467
Ala Thr Arg Ala Val Asp Ser Leu Ser Ile Asp Asn Ala Thr Trp Val
                430                 435                 440

ATG ACG GAC AAC TCG AAC GTC GGT GCG CTA CGG CTG GCC AGC GAC GGC        1515
Met Thr Asp Asn Ser Asn Val Gly Ala Leu Arg Leu Ala Ser Asp Gly
                445                 450                 455

AGC GTC GAT TTC CAG CAG CCG GCC GAA GCT GGG CGG TTC AAG GTC CTG        1563
Ser Val Asp Phe Gln Gln Pro Ala Glu Ala Gly Arg Phe Lys Val Leu
                460                 465                 470

ACG GTC AAT ACG CTG GCG GGT TCG GGG CTG TTC CGC ATG AAT GTC TTC        1611
Thr Val Asn Thr Leu Ala Gly Ser Gly Leu Phe Arg Met Asn Val Phe
                475                 480                 485

GCG GAC CTG GGG CTG AGC GAC AAG CTG GTC GTC ATG CAG GAC GCC AGC        1659
Ala Asp Leu Gly Leu Ser Asp Lys Leu Val Val Met Gln Asp Ala Ser
490                 495                 500                 505

GGC CAG CAC AGG CTG TGG GTC CGC AAC AGC GGC AGC GAG CCG GCC AGC        1707
Gly Gln His Arg Leu Trp Val Arg Asn Ser Gly Ser Glu Pro Ala Ser
                510                 515                 520

GCC AAC ACC CTG CTG CTG GTG CAG ACG CCA CTA GGC AGC GCG GCG ACC        1755
Ala Asn Thr Leu Leu Leu Val Gln Thr Pro Leu Gly Ser Ala Ala Thr
                525                 530                 535

TTT ACC CTT GCC AAC AAG GAC GGC AAG GTC GAT ATC GGT ACC TAT CGC        1803
Phe Thr Leu Ala Asn Lys Asp Gly Lys Val Asp Ile Gly Thr Tyr Arg
                540                 545                 550

TAT CGA TTG GCC GCC AAC GGC AAT GGG CAG TGG AGC CTG GTG GGC GCG        1851
Tyr Arg Leu Ala Ala Asn Gly Asn Gly Gln Trp Ser Leu Val Gly Ala
                555                 560                 565

AAG GCG CCG CCG GCG CCC AAG CCC GCG CCG CAG CCG GGT CCC CAG CCG        1899
Lys Ala Pro Pro Ala Pro Lys Pro Ala Pro Gln Pro Gly Pro Gln Pro
570                 575                 580                 585

CCG CAG CCG CCG CAG CCG CAG CCG GAA GCG CCG GCG CCG CAA CCG CCG        1947
Pro Gln Pro Pro Gln Pro Gln Pro Glu Ala Pro Ala Pro Gln Pro Pro
                590                 595                 600

GCG GGC AGG GAG TTG TCC GCC GCC GCC AAC GCG GCG GTC AAC ACG GGT        1995
Ala Gly Arg Glu Leu Ser Ala Ala Ala Asn Ala Ala Val Asn Thr Gly
                605                 610                 615

GGG GTG GGC CTG GCC AGC ACG CTC TGG TAC GCC GAA AGC AAT GCG TTG        2043
Gly Val Gly Leu Ala Ser Thr Leu Trp Tyr Ala Glu Ser Asn Ala Leu
                620                 625                 630

TCC AAG CGC CTG GGC GAG TTG CGC CTG AAT CCG GAC GCC GGC GGC GCC        2091
Ser Lys Arg Leu Gly Glu Leu Arg Leu Asn Pro Asp Ala Gly Gly Ala
                635                 640                 645
```

Fig. 1A-3

```
TGG GGC CGC GGC TTC GCG CAA CGC CAG CAG CTG GAC AAC CGC GCC GGG    2139
Trp Gly Arg Gly Phe Ala Gln Arg Gln Gln Leu Asp Asn Arg Ala Gly
650             655                 660                 665

CGG CGC TTC GAC CAG AAG GTG GCC GGC TTC GAG CTG GGC GCC GAC CAC    2187
Arg Arg Phe Asp Gln Lys Val Ala Gly Phe Glu Leu Gly Ala Asp His
                670                 675                 680

GCG GTG GCG GTG GCC GGC GGA CGC TGG CAC CTG GGC GGG CTG GCC GGC    2235
Ala Val Ala Val Ala Gly Gly Arg Trp His Leu Gly Gly Leu Ala Gly
                685                 690                 695

TAT ACG CGC GGC GAC CGC GGC TTC ACC GGC GAC GGC GGC GGC CAC ACC    2283
Tyr Thr Arg Gly Asp Arg Gly Phe Thr Gly Asp Gly Gly Gly His Thr
        700                 705                 710

GAC AGC GTG CAT GTC GGG GGC TAT GCC ACA TAT ATC GCC GAC AGC GGT    2331
Asp Ser Val His Val Gly Gly Tyr Ala Thr Tyr Ile Ala Asp Ser Gly
        715                 720                 725

TTC TAC CTG GAC GCG ACG CTG CGC GCC AGC CGC CTG GAG AAT GAC TTC    2379
Phe Tyr Leu Asp Ala Thr Leu Arg Ala Ser Arg Leu Glu Asn Asp Phe
730             735                 740                 745

AAG GTG GCG GGC AGC GAC GGG TAC GCG GTC AAG GGC AAG TAC CGC ACC    2427
Lys Val Ala Gly Ser Asp Gly Tyr Ala Val Lys Gly Lys Tyr Arg Thr
                750                 755                 760

CAT GGG GTG GGC GCC TCG CTC GAG GCG GGC CGG CGC TTT ACC CAT GCC    2475
His Gly Val Gly Ala Ser Leu Glu Ala Gly Arg Arg Phe Thr His Ala
                765                 770                 775

GAC GGC TGG TTC CTC GAG CCG CAG GCC GAG CTG GCG GTA TTC CGG GCC    2523
Asp Gly Trp Phe Leu Glu Pro Gln Ala Glu Leu Ala Val Phe Arg Ala
        780                 785                 790

GGC GGC GGT GCG TAC CGC GCG GCC AAC GGC CTG CGG GTG CGC GAC GAA    2571
Gly Gly Gly Ala Tyr Arg Ala Ala Asn Gly Leu Arg Val Arg Asp Glu
        795                 800                 805

GGC GGC AGC TCG GTG CTG GGT CGC CTG GGC CTG GAG GTC GGC AAG CGC    2619
Gly Gly Ser Ser Val Leu Gly Arg Leu Gly Leu Glu Val Gly Lys Arg
810             815                 820                 825

ATC GAA CTG GCA GGC GGC AGG CAG GTG CAG CCA TAC ATC AAG GCC AGC    2667
Ile Glu Leu Ala Gly Gly Arg Gln Val Gln Pro Tyr Ile Lys Ala Ser
                830                 835                 840

GTG CTG CAG GAG TTC GAC GGC GCG GGT ACG GTA CAC ACC AAC GGC ATC    2715
Val Leu Gln Glu Phe Asp Gly Ala Gly Thr Val His Thr Asn Gly Ile
                845                 850                 855

GCG CAC CGC ACC GAA CTG CGC GGC ACG CGC GCC GAA CTG GGC CTG GGC    2763
Ala His Arg Thr Glu Leu Arg Gly Thr Arg Ala Glu Leu Gly Leu Gly
        860                 865                 870
```

*Fig. 1A-4*

```
ATG GCC GCC GCG CTG GGC CGC GGC CAC AGC CTG TAT GCC TCG TAC GAG        2811
Met Ala Ala Ala Leu Gly Arg Gly His Ser Leu Tyr Ala Ser Tyr Glu
    875                 880                 885

TAC TCC AAG GGC CCG AAG CTG GCC ATG CCG TGG ACC TTC CAC GCG GGC        2859
Tyr Ser Lys Gly Pro Lys Leu Ala Met Pro Trp Thr Phe His Ala Gly
890                 895                 900                 905

TAC CGG TAC AGC TGG TAAAGCGAGG AGGGTCTATC CCCCGCGGAG GAGTTTTTCC        2914
Tyr Arg Tyr Ser Trp
                910

TGGAGCTTGG CCGGTGCCAG TCTCCAGGCT CAGGCGGCCA GGGCCTGCGG GCCGGGCAGG     2974

CCGCGCTGGT GCTGGCCGAA CCATTG                                          3000
```

*Fig. 1A-5*

```
ATCGATGATG CGTCGCTGTA ACACGGCAAA TACCGTGCAT TGCAGCGGTT CTGGATGGCG      60

TTCTTCGTAC GTTTGCTGCG CCCATTCTTC CCTGTTCCAT CGCGGTGCGG CCATGGCGGG     120

CGTCTGCTCT TCACCCGGCA TCCA ATG AAC ATG TCT CTG TCA CGC ATT GTC        171
              Met Asn Met Ser Leu Ser Arg Ile Val
                1                   5

TTG GCG GCG CCC CTG CGC CGC ACC ACA CTG GCC ATG GCG CTG GGC GCG       219
Leu Ala Ala Pro Leu Arg Arg Thr Thr Leu Ala Met Ala Leu Gly Ala
 10              15                  20                  25
                                   ↓
CTG GGC GCC GCG CCC GCC GCG TAC GCC GAC TGG AAC AAC CAG TCC ATC       267
Leu Gly Ala Ala Pro Ala Ala Tyr Ala Asp Trp Asn Asn Gln Ser Ile
             30                  35                  40

ATC AAG GCC GGC GAG CGC CAG CAC GGC ATC CAC ATC AAG CAA AGC GAT       315
Ile Lys Ala Gly Glu Arg Gln His Gly Ile His Ile Lys Gln Ser Asp
             45                  50                  55

GGC GCC GGC GTA CGG ACC GCC ACC GGA ACG ACC ATC AAG GTA AGC GGT       363
Gly Ala Gly Val Arg Thr Ala Thr Gly Thr Thr Ile Lys Val Ser Gly
             60                  65                  70

CGT CAG GCC CAG GGC GTC CTG CTG GAA AAT CCC GCG GCC GAG CTG CGG       411
Arg Gln Ala Gln Gly Val Leu Leu Glu Asn Pro Ala Ala Glu Leu Arg
 75              80                  85

TTC CAG AAC GGC AGC GTC ACG TCT TCG GGA CAG CTG TTC GAC GAA GGC       459
Phe Gln Asn Gly Ser Val Thr Ser Ser Gly Gln Leu Phe Asp Glu Gly
 90              95                  100                 105

GTC CGG CGC TTT CTG GGC ACC GTC ACC GTC AAG GCC GGC AAG CTG GTC       507
Val Arg Arg Phe Leu Gly Thr Val Thr Val Lys Ala Gly Lys Leu Val
             110                 115                 120

GCC GAT CAC GCC ACG CTG GCC AAC GTC AGC GAC ACC CGG GAC GAC GAC       555
Ala Asp His Ala Thr Leu Ala Asn Val Ser Asp Thr Arg Asp Asp Asp
             125                 130                 135

GGC ATC GCG CTC TAT GTG GCC GGC GAG CAG GCC CAG GCC AGC ATC GCC       603
Gly Ile Ala Leu Tyr Val Ala Gly Glu Gln Ala Gln Ala Ser Ile Ala
             140                 145                 150

GAC AGC ACC CTG CAG GGC GCG GGC GGC GTG CGG GTC GAG CGC GGC GCC       651
Asp Ser Thr Leu Gln Gly Ala Gly Gly Val Arg Val Glu Arg Gly Ala
 155                 160                 165

AAT GTC ACG GTC CAA CGC AGC ACC ATC GTT GAC GGG GGC TTG CAT ATC       699
Asn Val Thr Val Gln Arg Ser Thr Ile Val Asp Gly Gly Leu His Ile
 170                 175                 180                 185

GGC ACC CTG CAG CCG CTG CAG CCG GAA GAC CTT CCG CCC AGC CGG GTG       747
Gly Thr Leu Gln Pro Leu Gln Pro Glu Asp Leu Pro Pro Ser Arg Val
             190                 195                 200
```

*Fig. 1B-1*

```
GTG CTG GGC GAC ACC AGC GTG ACC GCC GTG CCC GCC AGC GGC GCG CCC        795
Val Leu Gly Asp Thr Ser Val Thr Ala Val Pro Ala Ser Gly Ala Pro
            205                 210                 215

GCG GCG GTG TCT GTA TTC GGG GCC AAT GAG CTT ACG GTT GAT GGC GGG        843
Ala Ala Val Ser Val Phe Gly Ala Asn Glu Leu Thr Val Asp Gly Gly
            220                 225                 230

CAC ATC ACC GGG GGG CGG GCA GCG GGG GTG GCG GCC ATG GAC GGG GCG        891
His Ile Thr Gly Gly Arg Ala Ala Gly Val Ala Ala Met Asp Gly Ala
            235                 240                 245

ATC GTG CAT CTG CAG CGC GCG ACG ATA CGG CGG GGG GAC GCG CCT GCC        939
Ile Val His Leu Gln Arg Ala Thr Ile Arg Arg Gly Asp Ala Pro Ala
250             255                 260                 265

GGC GGT GCG GTT CCA GGC GGT GCT GTT CCC GGC GGC TTC GGC CCC CTC        987
Gly Gly Ala Val Pro Gly Gly Ala Val Pro Gly Gly Phe Gly Pro Leu
            270                 275                 280

CTT GAC GGC TGG TAT GGC GTG GAT GTA TCG GAT TCC ACC GTG GAC CTC       1035
Leu Asp Gly Trp Tyr Gly Val Asp Val Ser Asp Ser Thr Val Asp Leu
            285                 290                 295

GCT CAG TCG ATC GTC GAG GCG CCG CAG CTG GGC GCC GCG ATC CGG GCG       1083
Ala Gln Ser Ile Val Glu Ala Pro Gln Leu Gly Ala Ala Ile Arg Ala
            300                 305                 310

GGC CGC GGC GCC AGG GTG ACG GTG TCG GGC GGC AGC TTG TCC GCA CCG       1131
Gly Arg Gly Ala Arg Val Thr Val Ser Gly Gly Ser Leu Ser Ala Pro
            315                 320                 325

CAC GGC AAT GTC ATC GAG ACC GGC GGC GGC GCG CGT CGC TTC CCG CCT       1179
His Gly Asn Val Ile Glu Thr Gly Gly Gly Ala Arg Arg Phe Pro Pro
330                 335                 340                 345

CCG GCC TCG CCC CTG TCG ATC ACC TTG CAG GCG GGC GCA CGG GCG CAG       1227
Pro Ala Ser Pro Leu Ser Ile Thr Leu Gln Ala Gly Ala Arg Ala Gln
                350                 355                 360

GGG AGG GCG CTG CTG TAC CGG GTC CTG CCG GAG CCC GTG AAG CTG ACG       1275
Gly Arg Ala Leu Leu Tyr Arg Val Leu Pro Glu Pro Val Lys Leu Thr
                365                 370                 375

CTG GCG GGC GGC GCC CAG GGG CAG GGC GAC ATC GTC GCG ACG GAG CTG       1323
Leu Ala Gly Gly Ala Gln Gly Gln Gly Asp Ile Val Ala Thr Glu Leu
                380                 385                 390

CCT CCC ATT CCA GGC GCG TCG AGC GGG CCG CTC GAC GTG GCG CTG GCC       1371
Pro Pro Ile Pro Gly Ala Ser Ser Gly Pro Leu Asp Val Ala Leu Ala
            395                 400                 405

AGC CAG GCC CGA TGG ACG GGC GCT ACC CGC GCG GTC GAC TCG CTG TCC       1419
Ser Gln Ala Arg Trp Thr Gly Ala Thr Arg Ala Val Asp Ser Leu Ser
410                 415                 420                 425
```

*Fig. 1B-2*

```
ATC GAC AAC GCC ACC TGG GTC ATG ACG GAC AAC TCG AAC GTC GGC GCG     1467
Ile Asp Asn Ala Thr Trp Val Met Thr Asp Asn Ser Asn Val Gly Ala
            430                 435                 440

CTG CGG CTG GCC AGC GAC GGC AGC GTC GAT TTC CAG CAG CCG GCC GAA     1515
Leu Arg Leu Ala Ser Asp Gly Ser Val Asp Phe Gln Gln Pro Ala Glu
            445                 450                 455

GCT GGG CGG TTC AAG TGC CTG ATG GTC GAT ACG CTG GCG GGT TCG GGG     1563
Ala Gly Arg Phe Lys Cys Leu Met Val Asp Thr Leu Ala Gly Ser Gly
            460                 465                 470

CTG TTC CGC ATG AAT GTC TTC GCG GAC CTG GGG CTG AGC GAC AAG CTG     1611
Leu Phe Arg Met Asn Val Phe Ala Asp Leu Gly Leu Ser Asp Lys Leu
        475                 480                 485

GTC GTC ATG CGG GAC GCC AGC GGC CAG CAC AGG CTG TTG GTC CGC AAC     1659
Val Val Met Arg Asp Ala Ser Gly Gln His Arg Leu Leu Val Arg Asn
490                 495                 500                 505

AGC GGC AGC GAG CCG GCC AGC GGC AAC ACC ATG CTG CTG GTG CAG ACG     1707
Ser Gly Ser Glu Pro Ala Ser Gly Asn Thr Met Leu Leu Val Gln Thr
                510                 515                 520

CCA CGA GGC AGC GCG GCG ACC TTT ACC CTT GCC AAC AAG GAC GGC AAG     1755
Pro Arg Gly Ser Ala Ala Thr Phe Thr Leu Ala Asn Lys Asp Gly Lys
            525                 530                 535

GTC GAT ATC GGT ACC TAC CGC TAT CGA TTG GCC GCC AAC GGC AAT GGG     1803
Val Asp Ile Gly Thr Tyr Arg Tyr Arg Leu Ala Ala Asn Gly Asn Gly
            540                 545                 550

CAG TGG AGC CTG GTG GGC GCG AAG GCG CCG CCG GCG CCC AAG CCC GCG     1851
Gln Trp Ser Leu Val Gly Ala Lys Ala Pro Pro Ala Pro Lys Pro Ala
    555                 560                 565

CCG CAG CCC GGT CCC CAG CCC GGT CCC CAG CCG CCG CAG CCG CCG CAG     1899
Pro Gln Pro Gly Pro Gln Pro Gly Pro Gln Pro Pro Gln Pro Pro Gln
570                 575                 580                 585

CCG CCG CAG CCG CCA CAG AGG CAG CCG GAA GCG CCG GCG CCG CAA CCG     1947
Pro Pro Gln Pro Pro Gln Arg Gln Pro Glu Ala Pro Ala Pro Gln Pro
                590                 595                 600

CCG GCG GGC AGG GAG TTG TCC GCC GCC GCC AAC GCG GCG GTC AAC ACG     1995
Pro Ala Gly Arg Glu Leu Ser Ala Ala Ala Asn Ala Ala Val Asn Thr
            605                 610                 615

GGT GGG GTG GGC CTG GCC AGC ACG CTC TGG TAC GCC GAA AGC AAT GCG     2043
Gly Gly Val Gly Leu Ala Ser Thr Leu Trp Tyr Ala Glu Ser Asn Ala
            620                 625                 630

TTG TCC AAG CGC CTG GGC GAG TTG CGC CTG AAT CCG GAC GCC GGC GGC     2091
Leu Ser Lys Arg Leu Gly Glu Leu Arg Leu Asn Pro Asp Ala Gly Gly
        635                 640                 645
```

Fig. 1B-3

```
GCT TGG GGC CGC GGC TTC GCG CAA CGC CAG CAA CTG GAC AAC CGC GCC      2139
Ala Trp Gly Arg Gly Phe Ala Gln Arg Gln Gln Leu Asp Asn Arg Ala
650             655             660             665

GGG CGG CGC TTC GAC CAG AAG GTG GCC GGC TTC GAG CTG GGC GCC GAC      2187
Gly Arg Arg Phe Asp Gln Lys Val Ala Gly Phe Glu Leu Gly Ala Asp
                670             675             680

CAC GCG GTG GCG GTG GCC GGC GGG CGC TGG CAC CTG GGC GGG CTG GCC      2235
His Ala Val Ala Val Ala Gly Gly Arg Trp His Leu Gly Gly Leu Ala
            685             690             695

GGC TAT ACG CGC GGC GAC CGC GGC TTT ACC GGC GAC GGC GGC GGC CAC      2283
Gly Tyr Thr Arg Gly Asp Arg Gly Phe Thr Gly Asp Gly Gly Gly His
        700             705             710

ACC GAC AGC GTG CAT GTC GGG GGC TAT GCC ACC TAT ATC GCC AAC AGC      2331
Thr Asp Ser Val His Val Gly Gly Tyr Ala Thr Tyr Ile Ala Asn Ser
    715             720             725

GGT TTC TAC CTG GAC GCG ACG CTG CGC GCC AGC CGC CTC GAA AAT GAC      2379
Gly Phe Tyr Leu Asp Ala Thr Leu Arg Ala Ser Arg Leu Glu Asn Asp
730             735             740             745

TTC AAG GTG GCG GGC AGC GAT GGG TAC GCG GTC AAG GGC AAG TAC CGC      2427
Phe Lys Val Ala Gly Ser Asp Gly Tyr Ala Val Lys Gly Lys Tyr Arg
                750             755             760

ACC CAT GGG GTA GGC GCC TCG CTC GAG GCG GGC CGG CGC TTC GCC CAT      2475
Thr His Gly Val Gly Ala Ser Leu Glu Ala Gly Arg Arg Phe Ala His
            765             770             775

GCC GAC GGC TGG TTC CTC GAG CCG CAG GCC GAG CTG GCG GTG TTC CGG      2523
Ala Asp Gly Trp Phe Leu Glu Pro Gln Ala Glu Leu Ala Val Phe Arg
        780             785             790

GTC GGC GGC GGT TCG TAC CGC GCG GCC AAT GGC CTG CGG GTG CGC GAC      2571
Val Gly Gly Gly Ser Tyr Arg Ala Ala Asn Gly Leu Arg Val Arg Asp
    795             800             805

GAA GGC GGC AGC TCG GTG CTG GGT CGC CTG GGC CTG GAG GTC GGC AAG      2619
Glu Gly Gly Ser Ser Val Leu Gly Arg Leu Gly Leu Glu Val Gly Lys
810             815             820             825

CGC ATC GAA CTG GCA GGC GGC AGG CAG GTG CAG CCA TAC ATC AAG GCC      2667
Arg Ile Glu Leu Ala Gly Gly Arg Gln Val Gln Pro Tyr Ile Lys Ala
                830             835             840

AGC GTG CTG CAG GAG TTC GAC GGC GCG GGT ACG GTA CGC ACC AAC GGC      2715
Ser Val Leu Gln Glu Phe Asp Gly Ala Gly Thr Val Arg Thr Asn Gly
            845             850             855

ATC GCG CAC CGC ACC GAA CTG CGC GGC ACG CGC GCC GAA CTG GGC CTG      2763
Ile Ala His Arg Thr Glu Leu Arg Gly Thr Arg Ala Glu Leu Gly Leu
        860             865             870
```

Fig. 1B-4

```
GGC ATG GCC GCC GCG CTG GGC CGC GGC CAC AGC CTG TAT GCC TCG TAC        2811
Gly Met Ala Ala Ala Leu Gly Arg Gly His Ser Leu Tyr Ala Ser Tyr
    875                 880                 885

GAG TAC TCC AAG GGG CCG AAG CTG GCC ATG CCG TGG ACC TTC CAC GCG        2859
Glu Tyr Ser Lys Gly Pro Lys Leu Ala Met Pro Trp Thr Phe His Ala
890             895                 900                 905

GGC TAC CGG TAC AGC TGG TAAAGCGAGA AGGGTCCATC CCCCCGCGGG               2907
Gly Tyr Arg Tyr Ser Trp
                910

GGAGATTTTC CTGGAGGTTG GCCGGTGCCA GTCTCCAGGC TCAGGCGGCC AGGGCGTGCG      2967

GGCCGGGCAG GCCGTGCTGG TGCTGGCCGA ACC                                   3000
```

*Fig. 1B-5*

```
            ATGATG CGTCGCTGTA ACACGGCAAA TACCGTGCAT TGCAGCGGTT CTGGATGGCG    60

TTCTTCGTAC GTTTGCTGCG CCCATTCTTC CCTGTTCCAT CGCGGTGCGG GCATGGCGGG         120

CGTCTGCTCT TCACCCGGCA TCCA ATG AAC ATG TCT CTG TCA CGC ATT GTC            171
                          Met Asn Met Ser Leu Ser Arg Ile Val
                           1               5

AAG GCG GCG CCC CTG CGC CGC ACC ACA CTG GCC ATG GCG CTG GGC GCG           219
Lys Ala Ala Pro Leu Arg Arg Thr Thr Leu Ala Met Ala Leu Gly Ala
 10              15                  20                  25

CTG GGC GCC GCG CCC GCC GCG TAC GCC GAC TGG AAC AAC CAG TCC ATC           267
Leu Gly Ala Ala Pro Ala Ala Tyr Ala Asp Trp Asn Asn Gln Ser Ile
                 30                  35                  40

ATC AAG GCC GGC GAG CGC CAG CAC GGC ATC CAC ATC AAG CAA AGC GAT           315
Ile Lys Ala Gly Glu Arg Gln His Gly Ile His Ile Lys Gln Ser Asp
             45                  50                  55

GGC GCC GGC GTA CGG ACC GCC ACC GGA ACG ACC ATC AAG GTA AGC GGT           363
Gly Ala Gly Val Arg Thr Ala Thr Gly Thr Thr Ile Lys Val Ser Gly
         60                  65                  70

CGT CAG GCC CAG GGC GTC CTG CTG GAA AAT CCC GCG GCC GAG CTG CGG           411
Arg Gln Ala Gln Gly Val Leu Leu Glu Asn Pro Ala Ala Glu Leu Arg
     75                  80                  85

TTC CAG AAC GGC AGC GTC ACG TCT TCG GGA CAG CTG TTC GAC GAA GGC           459
Phe Gln Asn Gly Ser Val Thr Ser Ser Gly Gln Leu Phe Asp Glu Gly
 90                  95                 100                 105

GTC CGG CGC TTT CTG GGC ACC GTC ACC GTC AAG GCC GGC AAG CTG GTC           507
Val Arg Arg Phe Leu Gly Thr Val Thr Val Lys Ala Gly Lys Leu Val
                110                 115                 120

GCC GAT CAC GCC ACG CTG GCC AAC GTC AGC GAC ACC CGG GAC GAC GAC           555
Ala Asp His Ala Thr Leu Ala Asn Val Ser Asp Thr Arg Asp Asp Asp
            125                 130                 135

GGC ATC GCG CTC TAT GTG GCC GGC GAG CAG GCC CAG GCC AGC ATC GCC           603
Gly Ile Ala Leu Tyr Val Ala Gly Glu Gln Ala Gln Ala Ser Ile Ala
        140                 145                 150

GAC AGC ACC CTG CAG GGC GCG GGC GGC GTG CGG GTC GAG CGC GGC GCC           651
Asp Ser Thr Leu Gln Gly Ala Gly Gly Val Arg Val Glu Arg Gly Ala
    155                 160                 165

AAT GTC ACG GTC CAA CGC AGC ACC ATC GTT GAC GGG GGC TTG CAT ATC           699
Asn Val Thr Val Gln Arg Ser Thr Ile Val Asp Gly Gly Leu His Ile
170                 175                 180                 185

GGC ACC CTG CAG CCG CTG CAG CCG GAA GAC CTT CCG CCC AGC CGG GTG           747
Gly Thr Leu Gln Pro Leu Gln Pro Glu Asp Leu Pro Pro Ser Arg Val
                190                 195                 200
```

Fig. 1C-1

| | |
|---|---|
| GTG CTG GGC GAC ACC AGC GTG ACC GCC GTG CCC GCC AGC GGC GCG CCC<br>Val Leu Gly Asp Thr Ser Val Thr Ala Val Pro Ala Ser Gly Ala Pro<br>205 210 215 | 795 |
| GCG GCG GTG TTT GTA TTC GGG GCC AAT GAG CTT ACG GTT GAT GGC GGG<br>Ala Ala Val Phe Val Phe Gly Ala Asn Glu Leu Thr Val Asp Gly Gly<br>220 225 230 | 843 |
| CAC ATC ACC GGG GGG CGG GCA GCG GGG GTG GCG GCC ATG GAC GGG GCG<br>His Ile Thr Gly Gly Arg Ala Ala Gly Val Ala Ala Met Asp Gly Ala<br>235 240 245 | 891 |
| ATC GTG CAT CTG CAG CGC GCG ACG ATA CGG CGG GGG GAC GCG CCT GCC<br>Ile Val His Leu Gln Arg Ala Thr Ile Arg Arg Gly Asp Ala Pro Ala<br>250 255 260 265 | 939 |
| GGC GGT GCG GTT CCA GGC GGT GCG GTT CCC GGC GGT GCC GTT CCC GGC<br>Gly Gly Ala Val Pro Gly Gly Ala Val Pro Gly Gly Ala Val Pro Gly<br>270 275 280 | 987 |
| GGC TTC GGC CCC CTC CTT GAC GGC TGG TAT GGC GTG GAT GTA TCG GAC<br>Gly Phe Gly Pro Leu Leu Asp Gly Trp Tyr Gly Val Asp Val Ser Asp<br>285 290 295 | 1035 |
| TCC ACC GTG GAC CTC GCT CAG TCG ATC GTC GAG GCG CCG CAG CTG GGC<br>Ser Thr Val Asp Leu Ala Gln Ser Ile Val Glu Ala Pro Gln Leu Gly<br>300 305 310 | 1083 |
| GCC GCG ATC CGG GCG GGC CGC GGC GCC AGG GTG ACG GTG TCG GGC GGC<br>Ala Ala Ile Arg Ala Gly Arg Gly Ala Arg Val Thr Val Ser Gly Gly<br>315 320 325 | 1131 |
| AGC TTG TCC GCA CCG CAC GGC AAT GTC ATC GAG ACC GGC GGC GGT GCG<br>Ser Leu Ser Ala Pro His Gly Asn Val Ile Glu Thr Gly Gly Gly Ala<br>330 335 340 345 | 1179 |
| CGT CGC TTC CCG CCT CCG GCC TCG CCC CTG TCG ATC ACC TTG CAG GCG<br>Arg Arg Phe Pro Pro Pro Ala Ser Pro Leu Ser Ile Thr Leu Gln Ala<br>350 355 360 | 1227 |
| GGC GCA CGG GCG CAG GGG AGG GCG CTG CTG TAC CGG GTC CTG CCG GAG<br>Gly Ala Arg Ala Gln Gly Arg Ala Leu Leu Tyr Arg Val Leu Pro Glu<br>365 370 375 | 1275 |
| CCC GTG AAG CTG ACG CTG GCG GGC GGC GCC CAG GGG CAG GGC GAC ATC<br>Pro Val Lys Leu Thr Leu Ala Gly Gly Ala Gln Gly Gln Gly Asp Ile<br>380 385 390 | 1323 |
| GTC GCG ACG GAG CTG CCT CCC ATT CCA GGC GCG TCG AGC GGG CCG CTC<br>Val Ala Thr Glu Leu Pro Pro Ile Pro Gly Ala Ser Ser Gly Pro Leu<br>395 400 405 | 1371 |
| GAC GTG GCG CTG GCC AGC CAG GCC CGA TGG ACG GGC GCT ACC CGC GCG<br>Asp Val Ala Leu Ala Ser Gln Ala Arg Trp Thr Gly Ala Thr Arg Ala<br>410 415 420 425 | 1419 |

*Fig. 1C-2*

| | |
|---|---|
| GTC GAC TCG CTG TCC ATC GAC AAC GCC ACC TGG GTC ATG ACG GAC AAC<br>Val Asp Ser Leu Ser Ile Asp Asn Ala Thr Trp Val Met Thr Asp Asn<br>430 435 440 | 1467 |
| TCG AAC GTC GGC GCG CTG CGG CTG GCC AGC GAC GGC AGC GTC GAT TTC<br>Ser Asn Val Gly Ala Leu Arg Leu Ala Ser Asp Gly Ser Val Asp Phe<br>445 450 455 | 1515 |
| CAG CAG CCG GCC GAA GCT GGG CGG TTC AAG GTC CTG ATG GTC GAT ACG<br>Gln Gln Pro Ala Glu Ala Gly Arg Phe Lys Val Leu Met Val Asp Thr<br>460 465 470 | 1563 |
| CTG GCG GGT TCG GGG CTG TTC CGC ATG AAT GTC TTC GCG GAC CTG GGG<br>Leu Ala Gly Ser Gly Leu Phe Arg Met Asn Val Phe Ala Asp Leu Gly<br>475 480 485 | 1611 |
| CTG AGC GAC AAG CTG GTC GTC ATG CGG GAC GCC AGC GGC CAG CAC AGG<br>Leu Ser Asp Lys Leu Val Val Met Arg Asp Ala Ser Gly Gln His Arg<br>490 495 500 505 | 1659 |
| CTG TGG GTC CGC AAC AGC GGC AGC GAG CCG GCC AGC GGC AAC ACC ATG<br>Leu Trp Val Arg Asn Ser Gly Ser Glu Pro Ala Ser Gly Asn Thr Met<br>510 515 520 | 1707 |
| CTG CTG GTG CAG ACG CCA CGA GGC AGC GCG GCG ACC TTT ACC CTT GCC<br>Leu Leu Val Gln Thr Pro Arg Gly Ser Ala Ala Thr Phe Thr Leu Ala<br>525 530 535 | 1755 |
| AAC AAG GAC GGC AAG GTC GAT ATC GGT ACC TAC CGC TAT CGA TTG GCC<br>Asn Lys Asp Gly Lys Val Asp Ile Gly Thr Tyr Arg Tyr Arg Leu Ala<br>540 545 550 | 1803 |
| GCC AAC GGC AAT GGG CAG TGG AGC CTG GTG GGC GCG AAG GCG CCG CCG<br>Ala Asn Gly Asn Gly Gln Trp Ser Leu Val Gly Ala Lys Ala Pro Pro<br>555 560 565 | 1851 |
| GCG CCC AAG CCC GCG CCG CAG CCC GGT CCC CAG CCC GGT CCC CAG CCG<br>Ala Pro Lys Pro Ala Pro Gln Pro Gly Pro Gln Pro Gly Pro Gln Pro<br>570 575 580 585 | 1899 |
| CCG CAG CCG CCG CAG CCG CCG CAG CCG CCG CAG CCG CCG CAG CCG CCA<br>Pro Gln Pro Pro Gln Pro Pro Gln Pro Pro Gln Pro Pro Gln Pro Pro<br>590 595 600 | 1947 |
| CAG AGG CAG CCG GAA GCG CCG GCG CCG CAA CCG CCG GCG GGC AGG GAG<br>Gln Arg Gln Pro Glu Ala Pro Ala Pro Gln Pro Pro Ala Gly Arg Glu<br>605 610 615 | 1995 |
| TTG TCC GCC GCC GCC AAC GCG GCG GTC AAC ACG GGT GGG GTG GGC CTG<br>Leu Ser Ala Ala Ala Asn Ala Ala Val Asn Thr Gly Gly Val Gly Leu<br>620 625 630 | 2043 |
| GCC AGC ACG CTC TGG TAC GCC GAA AGC AAT GCG TTG TCC AAG CGC CTG<br>Ala Ser Thr Leu Trp Tyr Ala Glu Ser Asn Ala Leu Ser Lys Arg Leu<br>635 640 645 | 2091 |

Fig. 1C-3

| | |
|---|---|
| GGC GAG TTG CGC CTG AAT CCG GAC GCC GGC GGC GCT TGG GGC CGC GGC<br>Gly Glu Leu Arg Leu Asn Pro Asp Ala Gly Gly Ala Trp Gly Arg Gly<br>650                655                660                665 | 2139 |
| TTC GCG CAA CGC CAG CAA CTG GAC AAC CGC GCC GGG CGG CGC TTC GAC<br>Phe Ala Gln Arg Gln Gln Leu Asp Asn Arg Ala Gly Arg Arg Phe Asp<br>                    670                675                680 | 2187 |
| CAG AAG GTG GCC GGC TTC GAG CTG GGC GCC GAC CAC GCG GTG GCG GTG<br>Gln Lys Val Ala Gly Phe Glu Leu Gly Ala Asp His Ala Val Ala Val<br>            685                690                695 | 2235 |
| GCC GGC GGG CGC TGG CAC CTG GGC GGG CTG GCC GGC TAT ACG CGC GGC<br>Ala Gly Gly Arg Trp His Leu Gly Gly Leu Ala Gly Tyr Thr Arg Gly<br>        700                705                710 | 2283 |
| GAC CGC GGC TTT ACC GGC GAC GGC GGC GGC CAC ACC GAC AGC GTG CAT<br>Asp Arg Gly Phe Thr Gly Asp Gly Gly Gly His Thr Asp Ser Val His<br>        715                720                725 | 2331 |
| GTC GGG GGC TAT GCC ACC TAT ATC GCC AAC AGC GGT TTC TAC CTG GAC<br>Val Gly Gly Tyr Ala Thr Tyr Ile Ala Asn Ser Gly Phe Tyr Leu Asp<br>730                735                740                745 | 2379 |
| GCG ACG CTG CGC GCC AGC CGC CTC GAA AAT GAC TTC AAG GTG GCG GGC<br>Ala Thr Leu Arg Ala Ser Arg Leu Glu Asn Asp Phe Lys Val Ala Gly<br>                    750                755                760 | 2427 |
| AGC GAT GGG TAC GCG GTC AAG GGC AAG TAC CGC ACC CAT GGG GTA GGC<br>Ser Asp Gly Tyr Ala Val Lys Gly Lys Tyr Arg Thr His Gly Val Gly<br>            765                770                775 | 2475 |
| GTC TCG CTC GAG GCG GGC CGG CGC TTC GCC CAT GCC GAC GGC TGG TTC<br>Val Ser Leu Glu Ala Gly Arg Arg Phe Ala His Ala Asp Gly Trp Phe<br>        780                785                790 | 2523 |
| CTC GAG CCG CAG GCC GAG CTG GCG GTG TTC CGG GTC GGC GGC GGT GCG<br>Leu Glu Pro Gln Ala Glu Leu Ala Val Phe Arg Val Gly Gly Gly Ala<br>    795                800                805 | 2571 |
| TAC CGC GCG GCC AAT GGC CTG CGG GTG CGC GAC GAA GGC GGC AGC TCG<br>Tyr Arg Ala Ala Asn Gly Leu Arg Val Arg Asp Glu Gly Gly Ser Ser<br>810                815                820                825 | 2619 |
| GTG CTG GGT CGC CTG GGC CTG GAG GTC GGC AAG CGC ATC GAA CTG GCA<br>Val Leu Gly Arg Leu Gly Leu Glu Val Gly Lys Arg Ile Glu Leu Ala<br>                    830                835                840 | 2667 |
| GGC GGC AGG CAG GTG CAG CCA TAC ATC AAG GCC AGC GTG TTG CAG GAG<br>Gly Gly Arg Gln Val Gln Pro Tyr Ile Lys Ala Ser Val Leu Gln Glu<br>            845                850                855 | 2715 |
| TTC GAC GGC GCG GGT ACG GTA CGC ACC AAC GGC ATC GCG CAT CGC ACC<br>Phe Asp Gly Ala Gly Thr Val Arg Thr Asn Gly Ile Ala His Arg Thr<br>        860                865                870 | 2763 |

Fig. 1C-4

```
GAA CTG CGC GGC ACG CGC GCC GAA CTG GGC CTG GGC ATG GCC GCC GCG    2811
Glu Leu Arg Gly Thr Arg Ala Glu Leu Gly Leu Gly Met Ala Ala Ala
    875                 880                 885

CTG GGC CGC GGC CAC AGC CTG TAT GCC TCG TAC GAG TAC TCC AAG GGC    2859
Leu Gly Arg Gly His Ser Leu Tyr Ala Ser Tyr Glu Tyr Ser Lys Gly
890                 895                 900                 905

CCG AAG CTG GCC ATG CCG TGG ACC TTC CAC GCG GGC TAC CGG TAC AGC    2907
Pro Lys Leu Ala Met Pro Trp Thr Phe His Ala Gly Tyr Arg Tyr Ser
                910                 915                 920

TGG TAAAGCGAGA AGGGTCCATC CCCCGCGGAG GAGTTTTTCC TGGAGGTTGG         2960
Trp

CCGGTGCCAG TCTCCAGGCT CAGGCGGCCA GGGCCTGCGG                        3000
```

Fig. 1C-5

| EcoRI | AvaI-315 | (BglII-1979) |
GAATTCACATTCAGGGTTCTGACCCGGG---p69 GENE---GCCAACGCAGCTGTTAACACT-

-GGTGGTGTAGGCCTTGCAAGTACTCTGTGGTACGCTGAATCTAATGCATTATCTTAAGGATCCGCTAGC
                                                                  NheI

TRANSFORMED PICHIA EXPRESSING THE PERTACTIN ANTIGEN

This is a continuation of U.S. application Ser. No. 08/305,792, filed Sep. 13, 1994, now abandoned, which is a continuation of U.S. application Ser. No. 07/937,822, filed Oct. 20, 1992, now abandoned, which was the National Stage of International Application No. PCT/GB91/00487, filed Mar. 28, 1991.

The present invention relates to the expression of heterologous protein in yeast, more particularly to the production of Bordetella pertactin antigens in Pichia, novel expression vectors containing the DNA sequences, and Pichia strains transformed therewith.

Bordetella pertussis causes whooping cough, an acute respiratory disease which is serious and debilitating in humans, children being particularly susceptible. The organism is responsible for approximately 1 million deaths each year, although this is being to some extent controlled in the developed countries by large scale immunisation programmes. It has been found hat immunisation against B. pertussis is very effective at preventing the disease, and that failure to vaccinate does lead to increased incidence of the disease. In practically all areas, immunisation is effected using a whole cell B. Pertussis vaccine which has been found to be relatively effective in preventing the disease and infant mortality.

However, public acceptance of whole cell vaccines has decreased due to side-effects and controversy over rare neurological complications attributed to such vaccine preparations. Consequently, researchers have been looking for safer, effective, acellular vaccines consisting of purified Bordetella antigens.

Surface antigen of B. pertussis is known to elicit a humoral and a cellular immune response in humans. It is disclosed as ACAP in European Patent Application published under No. 162639 and is now known as P.69 (I. G. Charles et al. Proc. Natl. Acad. Sci. USA, vol. 80, 3554–3558 (1989)). It is likely to be an important component of any future acellular vaccine against B. pertussis infections.

B. parapertussis and B. bronchiseptica are closely related to the B. pertussis organism. B. parapertussis is also responsible for outbreaks of whooping cough in man (Zeuler et al. J. pediatr. 9:493–497 (1946); B. bronchiseptica is known to cause respiratory diseases in animals, particularly atrophic rhinitis in pigs (Harris and Switzer Am. J. Vet. Res. 29 777–785 (1968)).

B. parapertussis and B. bronchiseptica appear to present antigens related to B. pertussis P.69. with molecular masses of 70 and 68 kDa respectively. These Bordetella antigens, which are referred to hereinafter as 'pertactin antigens', are known to bind to the BB05 antibody but appear to have different immunogenic properties (I. G. Charles et al. Proc. Natl. Acad. Sci. USA Vol. 80 3554–3558 (1989)). Only small amounts of pertactin antigen can be isolated from cultures of Bordetella organism. It is preferable for the production of antigens on a commercial scale, to be able to produce large quantities.

E. coli is known as a host organism for the manufacture of heterologous proteins such as antigens, in quantity, but has certain drawbacks since it contains toxic pyrogenic factors (lipopolysaccharides from the cell wall) which must be rigorously excluded from the final product. The ease with which these factors may be excluded will depend on the method of purification. However, it would be advantageous to eliminate the possibility of contamination altogether simply by using a non-toxic organism as the host, such as yeast.

When baker's yeast, Saccharomyces cerevisiae, is used as the host organism, poor expression levels of heterologous protein are frequently obtained. (Kingsman, et al., Biotechnology & Genet. Engin. Reviews. Vol. 3 377–416, 1985). Use of the yeast Pichia pastoris as a host for the expression of heterologous protein is also known (European Patent Publication Nos. 0180899 and 0263311). However, expression of membrane proteins in yeast is generally problematic since these proteins can interact with yeast cell membranes causing toxic effects to the yeast cell and reduced product yields. Examples of such difficulties have been described and include the expression of polyoma virus middle-T antigen (Belsham, et al. Eur. J. Biochem. 156 413–421, 1986); expression of the bacterial membrane protein OmpA (Janowitz, et al. Gene 20, 347–358, 1982); and expression of influenza virus haemagglutinin (Jabbar, et al., Proc. Natl. Acad. Sci. USA 82, 2019–2023, 1985).

The present inventors have found a means of producing good levels of expression of the Bordetella pertactin antigens by culturing Pichia transformants containing at least one copy of the DNA encoding a pertactin antigen or an antigenic fragment thereof.

Accordingly, in a first aspect of the invention there is provided a Pichia microorganism transformed with DNA for the expression of a pertactin antigen whose amino acid sequence is at least 95% homologous with that set forth in FIGS. 1A, 1B or 1C (SEQ ID NO: 1,2 or 3), or an antigenic fragment thereof.

It is preferable if the amino acid sequence described above is at least 98% homologous with that set forth in FIGS. 1A, 1B or 1C (SEQ ID NO: 1, 2 or 3) or an antigenic fragment thereof.

A pertactin antigen from B. pertussis includes the antigen whose amino acid sequence is at least 95% homologous with, but is preferably substantially the same as, that set out in FIG. 1A (SEQ ID NO: 1). This antigen is denoted P.69. A pertactin antigen from B. bronchiseptica includes the antigen whose amino acid sequence is at least 95% homologous with, but is preferably substantially the same as, that set out in FIG. 1B (SEQ ID NO: 2). This antigen is denoted P.68. A pertactin antigen from B. parapertussis includes the antigen whose amino acid sequence at least 95% homologous with, but is preferably substantially the same as, that set out in FIG. 1C (SEQ ID NO: 3). This antigen is denoted P.70.

The DNA for the expression of a pertactin antigen may encode a larger precursor which has a molecular weight of approximately 94 kD and which is processed within the cell to the desired antigen. In the case of P.69 the precursor is approximately 93.5 kD. The DNA encoding it has been cloned and sequenced by Charles et al., (PNAS, 86, pp 3554–3558, (1989)). The precursor of the P.68 antigen of B. bronchiseptica is approximately 94 kD and the precursor for P.70 of B. parapertussis is approximately 95 kD.

Pichia microorganisms transformed with DNA for the expression of an antigenic fragment of a pertactin antigen are also encompassed by the invention. The fragments preferably contain no more than 50 amino acid residues. More preferably they contain between 5 and 25 residues. The fragments most preferably comprise a defined antigenically effective sequence which essentially consists of amino acid residues 547 to 552 of the P.69 protein of B. pertussis.

This sequence is: PGPQPP (SEQ ID NO: 4)

The corresponding sequence for other strains of B. pertussis and for strains of B. parapertussis and B. bronchiseptica can be readily determined by lining up the amino acid sequence of the P.69 antigen, the P.70 antigen or the P.68 antigen respectively with the P.69 sequence shown by Charles et al (1989) referred to hereinbefore.

The fragments described above also include a sequence which essentially consists of the amino acid residues 544 to 566 of the P.69 protein of B. pertussis.

This sequence is : APQPGPQPPQPPQPQPEAPAPQP (SEQ ID NO: 5)

This sequence and the corresponding sequence for the P.70 antigen of B. parapertussis and the P.68 antigen of B. bronchiseptica can be aligned. A further fragment of interest is a 60 kD fragment encoded by the C terminal end of the DNA for P.69 which has been identified by Charles et. al. (1989) referred to hereinbefore as encoding an antigenic fragment of P.69.

Transformation of the organism may be carried out by any known method in the literature (Beggs, Nature 275, 104–109 (1978)). It is preferable to use the sphaeroplast method described by Cregg et al., Bio/Technology 5 479–485 (1987). The Pichia organism is preferably transformed with an expression cassette. Expression cassettes include DNA sequences in addition to that encoding the sequence of interest, in this instance the DNA encoding a pertactin antigen, such as transcriptional and translational initiation and termination sequences. The cassette may also include regulatory (i.e. promoter) and/or selectable marker sequences. Such expression cassettes are well known in the art and it is well within the ability of the skilled man to construct them. The expression cassette may form part of a vector construct or a naturally-occurring plasmid.

In a preferred embodiment the vector construct used to transform Pichia cells contains the promoter from the methanol-inducible AOX1 gene to drive expression of the DNA encoding a pertactin antigen. In particular, the present invention provides the vector pPIC3-60.5K. This vector, digested with BglII, will integrate in the host chromosomal AOX1 locus. The resultant aox1 transformants have the Mut$^S$ (methanol-utilisation slow) phenotype and can therefore be selected.

In a preferred aspect of the invention there is provided a Pichia organism transformed with more than one copy of the DNA encoding a pertactin antigen or an antigenic fragment thereof preferably integrated in the Pichia chromosomal DNA. It is preferable for the organism to contain greater than 5 copies preferably greater than 10 copies and most preferably between 5 and 30 copies of the DNA encoding pertactin antigen or an antigenic fragment thereof.

Such transformants can produce up to 5% of cell protein as the desired protein. In optimal fermenter conditions, levels of up to 10% of cell protein can be produced as the heterologous antigen. At such levels the majority of the antigen is insoluble. This is advantageous since the material can be readily isolated, renatured, and purified from the insoluble fraction.

The preferred Pichia organism referred to above is *Pichia pastoris*.

The invention further provides a process for producing a pertactin antigen which comprises culturing a transformed Pichia microorganism of the present invention.

Culturing of the transformed microorganism is carried out by known methods in for example a yeast extract band medium using a shake flask. For optimal conditions it is preferable to use a fermenter equipped for monitoring pH, $O_2$, stir speed, temperature and or air flow, to control the cells' environment. The antigen produced by such methods can be isolated by centrifugation and purified by chromatography.

In order to obtain organisms containing more than one copy of the DNA encoding a pertactin antigen it is necessary to prepare a library of transformants using standard techniques for example as described by Cregg et al., Bio/Technology 5: 479–485 (1987). Transformants containing at least one integrated copy of the DNA encoding a pertactin antigen form approximately 10–20% of these transformants. Those containing multiple copies of the DNA are then identified by screening. Individual transformants are grown on microtitre plates, each microculture is then transferred onto nitrocellulose filters and probed by Southern Hybridisation using pertactin-specific DNA radiolabelled to high specific activity using random-primed labelling (Feinberg et al., (1989) Anal. Biochem., 132- 6–13). A weak signal indicates that transformants contain a single copy of the DNA, a stronger signal indicates that the transformant contains more than one copy of DNA. The filters can then be mapped with the microtitre plates to identify the desired multi-copy microculture(s).

The present invention therefore provides a process of producing a Pichia organism according to the invention comprising:

i) transforming a Pichia organism with a vector construct containing DNA encoding a pertactin antigen or a fragment thereof and a selectable marker, ii) screening Pichia cells by means of selectable marker to select a transformed organism, iii) screening said transformed organism to identify transformants containing said DNA or fragment thereof.

Another aspect of the invention provides a process for the enhanced production of pertactin antigen comprising:

a) transforming a Pichia organism with multiple vectors constructs containing DNA encoding a pertactin antigen or a fragment thereof operably linked to a promoter to drive expression of said DNA; and thereafter b) culturing the resultant transformed organism under suitable conditions to obtain production of the antigen encoded by the DNA.

The present invention will now be exemplified further with reference to the accompanying figures.

FIGURE LEGENDS

FIG. 1A–1–1A–5. The amino acid sequence of P.69 and the DNA sequence encoding P.69 from B. pertussis and its 93.5 kD precursor.

FIG. 1B–1–1B–5. The amino acid sequence of P.68 and the DNA sequence encoding P.68 from B. bronchiseptica and its 94 kD precursor.

FIG. 1C–1–1C–5. The amino acid sequence of P.70 and the DNA sequence encoding P.70 from B. bronchiseptica and its 95 kD precursor.

FIG. 2A. Construction of the vector pPIC3-60.5K.

Figure 2B:
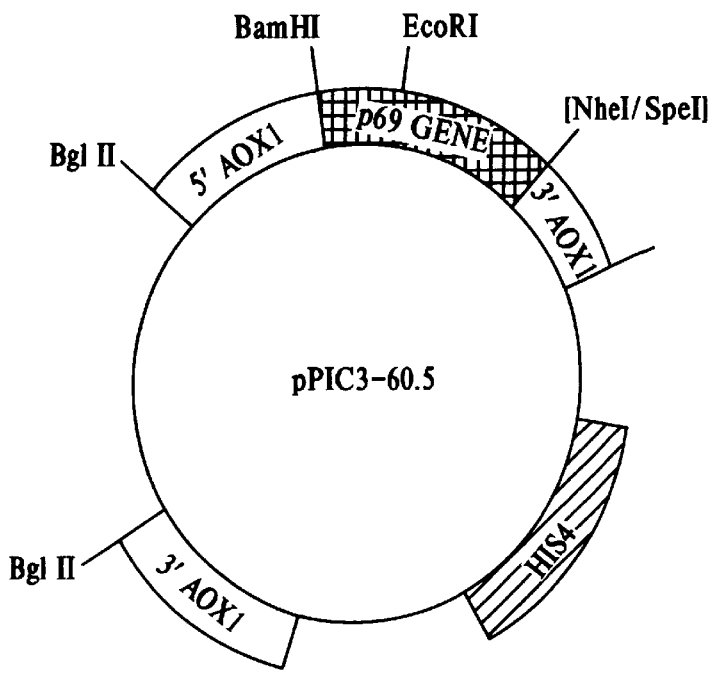

FIG. 2B. A plasmid map of the vector pPIC3-60.5K is shown in part A. Part B gives details of the DNA sequence of the DNA encoding P.69 that was used in the construction of pPIC3-60.5K. The EcoRI-NheI DNA fragment used contains the region from AvaI (nt.315) to BglI (nt.1979) from the 93 kD precursor gene (Charles et al. (1989), PNAS 86, 3554–3558), flanked by sequences derived from the vector pPERtac8 (Makoff et al. Bio/Technology 8,1030 (1990)). This fragment was inserted into pPic2 using the adapter oligonucleotides shown, which encode the 5' end of the DNA encoding P.69 gene.

Figure 3:
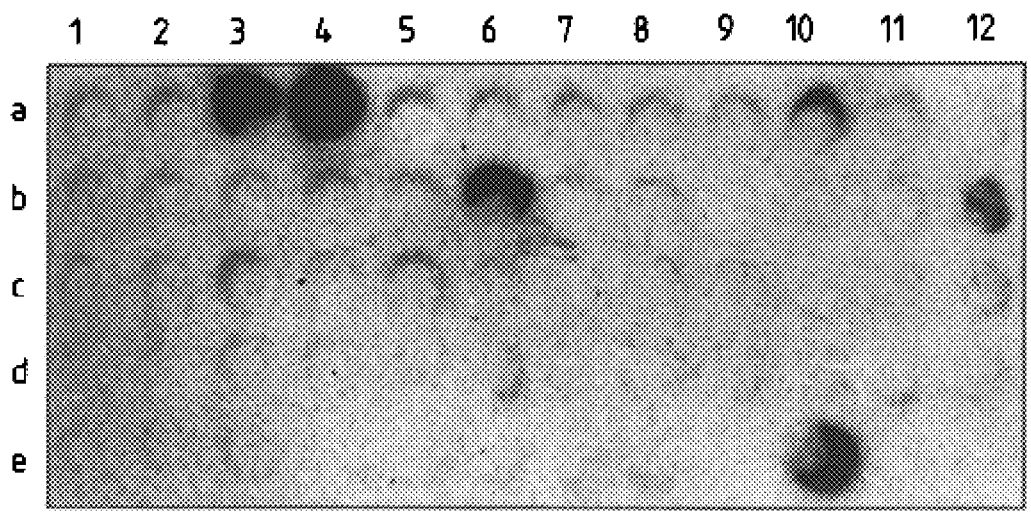

FIG. 3 DNA dot blot screen of GS115/pPIC3-60.5K Mut$^S$ transformants. The filter shown had 56 transformants, a positive control (position E10: multi-copy transformant SL 22, identified in a previous screen), and a negative control (E11: GS115). Most of the transformants in the screen gave a weak signal of similar intensity, a very small proportion gave a much stronger signal indicative of multi-copy integration (A3, A4, B6: designated nos. SL3, SL4 and SL18). Four further filters were screened in the same way, but no more multi-copy transformants were found.

Figure 4:
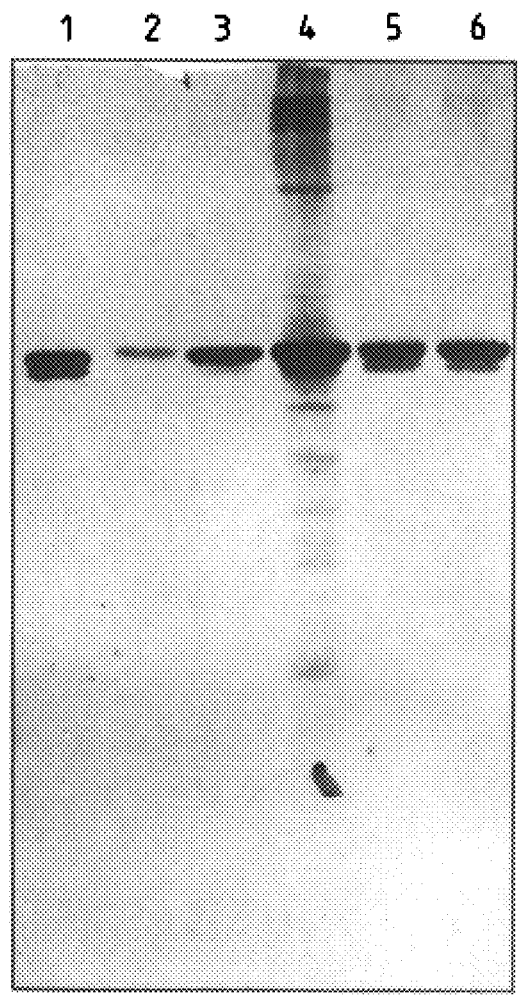

FIG. 4 Western blot analysis of P.69 pertactin induced P. pastoris cell extracts. P. pastoris transformants were induced for two days as described in Example 4. Proteins were separated by electrophoresis in 7.5% SDS-polyacrylamide gels and detected in Western blots using monoclonal antibody BB05 (Bio/Technology 8, 1030 (1990)). Tracks contained; authentic B. pertussis pertactin (1); or cell extracts from shake-flask induced; P. pastoris single-copy integrant SL1 (2), or from multi-copy integrant SL3 (3), SL4 (4), SL18 (5), and SL22 (6). Expression levels were estimated by comparison with known amounts of pertactin.

Figure 5:
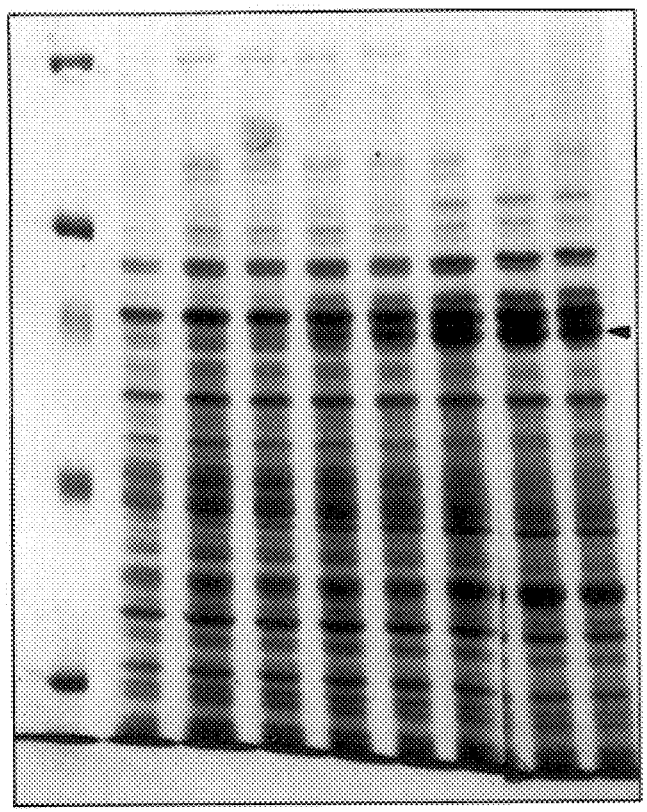

FIG. 5 Analysis of pertactin expression from a SL22 fermenter induction. A fermenter protocol of batch growth in glycerol, followed by glycerol-starvation, then a controlled methanol feed was used as described in Example 5. Protein extracts (50 µg) prepared from samples taken at different times after induction were analysed: tracks 2 to 9 correspond to −1, 0, 2, 4, 7, 23, 30, 50 hrs, respectively. Track 1 contained protein markers (Amersham Rainbow markers: myosin 200 kDa, phosphorylase b 92.5 kDa, bovine serum albumin 69 kDa, ovalbumin 46 kDa, carbonic anhydrase 30 kDa). The induced pertactin band is indicated by an arrow. Densitometric scanning of the stained gel (Joyce-Loebl, Chromoscan) indicated that pertactin reached approximately 10% of cell protein after 30 hrs.

Figure 6:
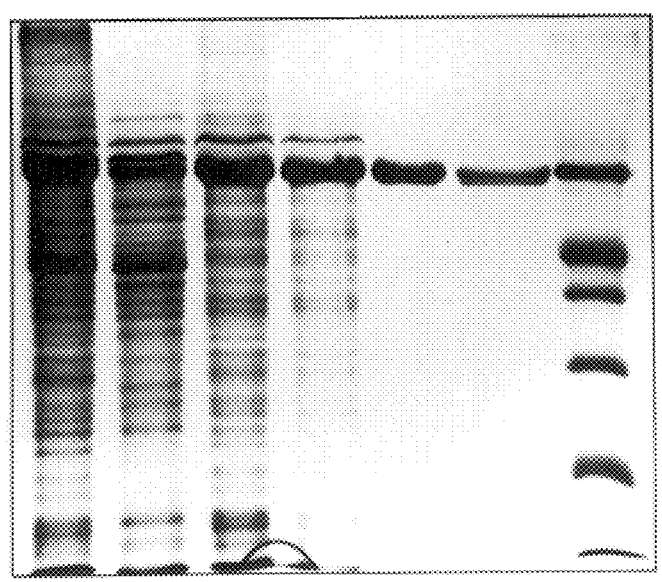

FIG. 6 SDS-polyacrylamide gel analysis of pertactin purification. Induced SL4 cells were harvested, suspended in buffer A (50 mM tris HCl pH8.0, 0.1M NaCl)+1% triton X-100, and lysed with glass beads using a Bead Beater (Biospec Products, Bartesville, Okla.). Insoluble protein was pelletted by centrifugation, washed and suspended in 6M guanidinium thiocyanate/buffer A. On dialysis pertactin remained soluble while yeast proteins could be removed by centrifugation. Solubilised pertactin was loaded onto a chelating Sepharose column charged with zinc and equilibrated with buffer A. After washing with 0.5M NaCl, pertactin was eluted in 50 mM MES pH6.0, 0.1M NaCl. Pertactin was further purified by chromatography on Q-sepharose in 50 mM tris HCl pH8.0, with elution using a 0 to 0.4M NaCl gradient. Gel tracks : [1] 30 µg total yeast protein [2] total soluble protein [3] guanidinium-solubilised fraction [4] Zn Sepharose-purified [5] Q-Sepharose-purified [6] native pertactin [7] Amersham Rainbow markers.

EXAMPLES

General information pertinent to the examples:
Media
YPD, 1 liter: 10 g yeast extract, 20 g peptone, 20 g glucose.
YNBBG, 1 liter: 13.4 g yeast nitrogen base w/o amino acids (Difco LABs., Detroit, Mich., USA), 0.4 mg biotin, 20 ml glycerol.
YNBBGCas: same as above plus 10 g casamino acids.
YNBBD: same as YNBBG but 20 g glucose instead of 20 ml glycerol.
YNBBM: same as YNBBG but 5 ml methanol instead of 20 ml glycerol.
YNBBDCas and YNBBMCas had 10 g casamino acids per liter.
Solid media: as above plus 20 g of agar per liter.

Example 1

Construction of *Pichia pastoris* Intracellular Expression Vectors for P.69

The vector pPIC3-60.5K, deposited at THE NATIONAL COLLECTION OF INDUSTRIAL AND MARINE BACTERIA LTD., P.O. Box 31, 135, Abbey Road, Aberdeen AB98DG, Scotland, UK on Mar. 30, 1990 under Accession No. 40270 in accordance with the terms of the Budapest Treaty derived from pAO804 (Digan et al, Dev. Ind. Microbiol. 1988 29, 59–65) was used for intracellular expression of P.69 in *Pichia pastoris*. This vector uses the promoter from the AOX1 gene to drive expression and can be integrated into the host chromosomal AOX1 locus. To facilitate insertion of the P.69 gene the synthetic oligonucleotides shown in FIG. 2A were cloned between the AsuII and EcoRI sites of pAO804, to give pPIC1. A derivative of this plasmid, pPIC2, which lacks the EcoRI site was then constructed. This was done by digesting with EcoRI followed by filling in of the protruding single stranded ends with the Klenow fragment of DNA polymerase I and ligating together the blunt ends. A 1.8 kb EcoRI-NheI fragment (see FIG. 2B) from the plasmid pPERtac8 (Makoff, et al, Bio/Technology 8, 1030 (1990)) which contains most of the gene encoding P.69 (a 60.5 kD polypeptide) was inserted into BamHI-SpeI cut pPIC2, using the adapter oligonucleotides shown in FIG. 2A, to give pPIC3-60.5K. These oligonucleotides encode the 5' end of the P.69 gene including the initiator ATG codon.

Example 2

Transformation of *Pichia pastoris*

*Pichia pastoris* strain GS115 (his4⁻) was transformed with pPIC3-60.5K using the sphaeroplast method described by Cregg et al., Bio/Technology 5: 479–485 (1987). Transformants were regenerated on minimal medium lacking histidine, so that His$^+$ colonies would be selected. The transforming DNA was 10 or 20 ug of BglII-digested pPIC3-60.5K. This digest contains two DNA fragments, one of which (7.2 kb) has AOX1 sequences at either end, so that it is targeted to integrate at and replace ('transplace') the chromosomal AOX1 gene.

The His$^+$ transformants generated are mainly found to contain undisrupted AOX1, and transplacements (aox1) may be isolated using a further screening procedure. Transplacements may be identified by their slow growth on methanol (Mut$^s$ as opposed to Mut$^+$ phenotype; Cregg et al., Bio/Technology 5 479–485, 1987). The transformants can be picked directly off regeneration plates and tested for growth on minimal methanol plates (YNBBM agar). Alternatively, the regeneration top agars can be lifted and homogenised in water and the yeast cells plated to about 300 colonies per plate on minimal glucose plates (YNBBD agar). Mut$^s$ colonies are then identified by replica-plating onto minimal methanol plates. In general, we and others have found the proportion of Mut$^s$ to be 10–20% of all the transformants. Occasionally Mut$^+$ transformants might be scored as Mut$^s$ and these may also prove to contain multiple copies of the vector.

Example 3

Screening for Multi-Copy Transformants

In order to screen large numbers of transformants rapidly, they were grown in individual wells in a 96-place sterile microtitre plate. 200 ul of YPD broth in each well was inoculated with a transformant, and the plates incubated for two days, at 30° C. without shaking, to ensure growth to stationary phase. Included on each microtitre plate was a well containing GS115 (negative control) and one containing a known pPIC3-60.5K integrant (positive control). Using a multi-channel pipetter, 50 ul samples of each micro-culture were transferred onto a nitrocellulose filter on a Schleicher & Schuell 'minifold' under vacuum. The filters were air dried, marked for orientation, then treated in the following way to lyse the cells: (i) 15 min at room temperature with 50 mM EDTA, 2.5% 2-mercaptoethanol pH9.0, (ii) 4 hrs at 37° C. with 1 mg/ml zymolyase (100T) in water, (iii) 5 min at room temperature in 0.1M NaOH, 1.5M NaCl and (iv) twice for 5 min at room temperature in 2×SSC. Each treatment was performed by soaking 2 sheets of 3 MM paper with the solution and placing the nitrocellulose filter on top. After these treatments the filters were baked at 80° C. for 1 hr.

The filters were probed by Southern hybridisation using P.69-specific DNA radiolabelled to high specific activity using random-primed labelling (Feinberg, A. and Vogelstein B., (1989), Anal. Biochem., 132, 6–13). Standard methods were used for prehybridisation, hybridisation, washing and autoradiography.

FIG. 3 shows the results of such a screen of over 200 $Mut^S$ transformants of pPIC3-60.5K. All the transformants reacted with the probe and most gave a similar weak signal (single-copy transformants), however, a very small proportion gave much stronger signals. These multi-copy transformants were tested further. The positive control in the filter shown is a transformant previously identified as multi-copy.

The copy number of the P.69 structural gene was determined by quantitative dot blot analysis of the DNA (Table 1). SL3, SL4 ($Mut^+$), SL18 and SL22 gave significantly higher levels of product than single-copy integrants, up to 5% of cell protein (Table 1). The majority (90%) of the pertactin produced by SL4 and SL22 was insoluble. SL 22 was deposited at NCIMB, Aberdeen, Scotland under Accession Number 40391 on Mar. 22, 1991, in accordance with the terms of the Budapest Treaty.

Example 4

Protein Analysis

Selected transformants were cultured in YNBBGCas for 2 days at 30° C. to reach stationary phase. These starter cultures were diluted to an $OD_{600}$ of 0.25 in 5 ml fresh YNBBGCas and grown for 6 hr. To induce these cultures the cells were collected by centrifugation, washed once in sterile water, and resuspended in YNBBMCas. Inductions were carried out for 2 days at 30° C.

Cells were then harvested by low speed centrifugation, washed once in water and suspended in 0.5 ml ice-cold break buffer (20 mM sodium phosphate pH7.0, 0.1% triton X-100, 4 mM phenylmethyl sulphonylfluoride). Acid washed glass beads (0.45 mm) were added and the cells were broken by vigorous vortexing. The protein concentration of the extracts was determined using the BioRad protein assay (BioRad, according to manufacturer's instructions) and the material was stored at −20° C.

Proteins were separated by electrophoresis in 7.5% SDS-polyacrylamide gels (Laemmli U.K., Nature 227: 680–785, 1970). The proteins were visualised in the gel by staining with Coomassie Brilliant Blue R. Alternatively the proteins were transferred to a nitrocellulose filter and reacted with the P.69 specific monoclonal antibody BB05 (Montaraz et al., 1985, Infect. Immunity 47, 744–751; deposited at PHLS Public Health Laboratory Service Centre for Applied Microbiology and Research, Porton Down, Salisbury, Wiltshire, U.K. in the European collection of Animal cell cultures under Accession No. 90020103, on Feb. 1, 1990 and under Accession No. 90010501, on 5th January, 1990 in accordance with the terms of the Budapest treaty), then with goat anti-mouse IgG conjugated to horse-radish peroxidase, and developed with $H_2O_2$ and 4-chloronaphthol (BioRad). In this way, the expressed P.69 could be specifically detected.

FIG. 4 shows a Western blot of induced extracts of four selected multi-copy transformants (SL 3, 4, 18 and 22) and one typical single-copy transformant. By comparison to standard concentrations of pure P.69, it can be estimated that single-copy transplacements express P.69 at 0.1–0.5% of total cell proteins (t.c.p.). SL22 at approx. 2%, and SL4 at approx. 5%. These levels are for shake flask induction conditions.

Example 5

Expression of P.69 During High Cell Density Fermentation

In optimal fermenter inductions an improvement in protein yield may be observed. Thus SL22 has been induced in a controlled fermenter (Example 5) and expresses P.69 at about 10% t.c.p. SL4, which was subsequently determined to be $Mut^+$ showed no change in expression levels in the fermenter. In low-expressing transformants the P.69 is largely soluble (approximately 55%), whereas at high expression levels it is mainly (approximately 90%) insoluble. This is preferable since the material can be readily isolated, renatured and purified from the insoluble fraction.

Production of P.69 by high cell density Pichia pastoris cultures was carried out using SL 22 in a 2L Braun fermenter equipped with monitors and controls for pH, dissolved $O_2$, stirring speed, temperature and air flow. A 10 ml YNBBG overnight culture was used to inoculate the fermenter containing 1 liter of 5×basal salts (phosphoric acid, 42 mls/L; calcium sulphate $2H_2O$, 1.8 g/L; potassium sulphate 28.6 g/L; magnesium sulphate $7H_2O$, 23.4 g/L; potassium hydroxide, 6.5 g/L) with 4 ml of $PTM_1$ salts (cupric sulphate $5H_2O$, 6 g/L; potassium iodide, 0.08 g/L; manganese sulphate $H_2O$, 3 g/L; sodium molybdate, 0.2 g/L; ferrous sulphate $7H_2O$, 65 h/L; biotin, 0.2 g/L; sulphuric acid, 5 ml/L) and 5% (v/v) glycerol at 30° C. Dissolved oxygen was maintained above 20% by adjusting aeration and agitation, and the pH was maintained at pH5.0 by the addition of 50% (v/v) ammonium hydroxide. Growth was continued until the glycerol was exhausted (24–30 hr). A limited glycerol feed (containing 50% w/v glycerol and 12 ml/L $PTM_1$ salts) was then initiated at 12 ml/hr for 17–21 hr. After this period the culture was induced by replacing the glycerol feed with a methanol feed (100% methanol plus 12 ml/L $PTM_1$ salts) at 1 ml/hr for 2 hr. Then the methanol feed rate was gradually increased over a period of 6 hr to 6 ml/hr and the fermentation was continued using these conditions for a further 40 hr. At this point the methanol feed rate was reduced to 2 ml/hr.

Samples were taken from the fermenter at different times after induction, and were analysed for P.69 expression as described in Example 4. The results of a Western blot analysis are shown in FIG. 5, indicating that levels of P.69 of about 10% of cell protein were achieved.

Example 6

Renaturation and Purification of P.69

Induced SL4 cells were harvested, suspended in buffer A (50 mM tris HCl pH8.0, 0.1M NaCl)+1% triton X-100, and lysed with glass beads using a Bead Beater (Biospec Products, Bartesville, Okla.). Insoluble protein was pelletted by centrifugation, washed and suspended in 6M guanidinium thiocyanate/buffer A. On dialysis pertactin remained soluble while yeast proteins could be removed by centregufation. Solubilised pertactin was loaded onto a chelating Sepharose column charged with zinc and equilibrated with buffer A. After washing with 0.5M NaCl, pertactin was eluted in 50 mM MES pH6.0, 0.1M NaCl. Pertactin was further purified by chromatography on Q-sepharose in 50 mM tris HCl pH8.0, with elution using a 0 to 0.4M NaCl gradient. Overall recovery of pertactin was 40%.

Example 7

Protection Data

Recombinant Pichia derived P.69 was tested for its ability to stimulate protection by toxoid in the Kendrick test, which is the standard international potency assay for whole-cell whooping cough vaccines.

Vaccines, containing 5 µg (TEST A) OR 20 µg (TEST B) of toxoid, 20 µg P.69 and 10% alhydrogel/PBS, were serially diluted in PBS and 0.5 ml doses were given intraperitoneally to male and female NIH/S mice.

Control mice received whole-cell vaccine (British ref. 66/84; top dose 8 IU/ml). After 14 days the mice were challenged intracerebrally with 20 µl. B. pertussis 18–323 (approximately 50LD$_{50}$).

Table 2 shows the results of two experiments, comparing toxoid with or without added P.69. Toxoid alone was clearly less protective than the whole-cell reference vaccine and could not be improved by increasing the dose from 5 µg to 20 µg. Addition of native or yeast-derived pertactin increased protection to the level of the whole-cell vaccine. For comparison, P.69 produced from E. coli (A. J. Makoff et al Bio/Technology 8, 1030 (1990)) was also included in the test and gave similar results. The results with pure recombinant P.69 from two different sources show that the immunogenic effect was due to P.69 itself, rather than contaminating B. pertussis antigens.

TABLE 1

Expression of P.69 pertactin in recombinant Pichia.

| Yeast/plasmid | Copy no.[a] | Expression level[b] (% cell protein) | Solubility |
|---|---|---|---|
| pPIC3-P69 (SL1,Mut$^s$) | 1 | 0.5% | 50% |
| pPIC3-P69 (SL18,Mut$^s$) | 12 | <2% | nd |

TABLE 1-continued

Expression of P.69 pertactin in recombinant Pichia.

| Yeast/plasmid | Copy no.[a] | Expression level[b] (% cell protein) | Solubility |
|---|---|---|---|
| pPIC3-P69 (SL3,Mut$^s$) | 13 | <2% | nd |
| pPIC3-P69 (SL22,Mut$^s$) | 21 | 2% (10%[c]) | <10% |
| pPIC3-P69 (SL4,Mut$^+$) | 30 | 5% (6%[c]) | <10% |

[a]The integrated vector copy numbers were determined accurately by dot blot analysis of purified DNA probed with radiolabelled P.69 structural DNA or DNA from the single-copy P. pastoris ARG4 (supplied by K. Shreekrishna, Phillips Petroleum Co.). A transformant known to be single-copy from Southern analysis was used as a control. Hybridised probe was measured by scintillation counting.
[b]Shake-flask inductions.
[c]Peak levels in fermenter inductions.

TABLE 2

| | Survivors after challenge[a] | | | |
|---|---|---|---|---|
| Antigen dilution | 1 | 1/4 | 1/16 | 1/64 |
| TEST A | | | | |
| Toxoid alone | 10 | 2 | 0 | 1 |
| Toxoid and native P.69 | 14 | 8 | 0 | 0 |
| Toxoid and E. coli recombinant P.69 | 17 | 8 | 1 | 0 |
| Reference vaccine | 15 | 7 | 1 | 1 |
| TEST B | | | | |
| Toxoid alone | 8 | 3[b] | 1 | 0 |
| Toxoid and native P.69 | 15 | 11 | 2 | 2 |
| Toxoid and Pichia recombinant P.69 | 15 | 10 | 3 | 0 |
| Reference vaccine | 15 | 7 | 2 | 1 |

[a]18 animals per group
[b]17 animals in this group

We claim:

1. A Pichia microorganism which expresses a pertactin antigen and which has multiple copies of DNA encoding the said antigen integrated into the chromosomal DNA thereof.

2. A Pichia microorganism according to claim 1, wherein the said antigen is the P69 antigen of *Bordetella pertussis*.

3. A Pichia microorganism according to claim 2, wherein the P69 antigen has the amino acid sequence shown in SEQ ID NO. 1.

4. A Pichia microorganism according to claim 1, wherein between 5 and 30 copies of the said DNA are integrated into the chromosomal DNA.

5. A Pichia microorganism according to claim 1, which is *Pichia pastoris*.

6. A process for producing a pertactin antigen, which process comprises the step of culturing a Pichia microorganism which expresses a pertactin antigen and which has multiple copies of DNA encoding the said antigen integrated into the chromosomal DNA thereof.

7. A process according to claim 6, wherein the said antigen is the P69 antigen of *Bordetella pertussis*.

8. A process according to claim 7, wherein the P69 antigen has the amino acid sequence shown in SEQ ID NO. 1.

9. A process according to claim 6, wherein between 5 and 30 copies of the said DNA are integrated into the chromosomal DNA.

10. A process according to claim 6, wherein the Pichia microorganism is *Pichia pastoris*.

11. A process according to claim 6, further comprising lysing the resultant Pichia microorganism and isolating pertactin antigen substantially free of Pichia proteins.

12. A process of claim 6, wherein said Pichia microorganism expresses the P69 antigen of *Bordella pertussis*, which antigen is coded for by a DNA containing the coding sequence of the P94 precursor of P69.

13. A process of claim 6, wherein said Pichia microorganism produces from 2%–5% pertactin of total cell protein.

14. A process of claim 6, wherein said Pichia microorganism produces from 2%–10% pertactin of total cell protein by weight.

15. A Pichia microorganism which expresses a pertactin antigen and which has multiple copies of a chromosomal locus integration vector comprising DNA encoding said antigen integrated into the chromosomal DNA thereof.

16. A Pichia microorganism according to claim 15, wherein the locus integration vector comprises AOX1 sequence effective to integrate into the AOX1 chromosomal locus.

17. A Pichia microorganism according to claim 15, wherein said locus integration vector is pPIC3-60.5k.

* * * * *

UNITED STATES PATENT AND TRADEMARK OFFICE
CERTIFICATE OF CORRECTION

PATENT NO.     : 6,197,548 B1
DATED          : March 6, 2001
INVENTOR(S)    : Jeffrey J. Clare et al.

It is certified that error appears in the above-identified patent and that said Letters Patent is hereby corrected as shown below:

Column 1,
Line 20, replace "hat" with -- that --.
Line 48, replace "P.69." with -- P.69, --.

Column 32,
Line 21, delete "by weight".

Signed and Sealed this

Eighteenth Day of March, 2003

JAMES E. ROGAN
*Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 2999 base pairs
       (B) TYPE: nucleic acid
       (C) STRANDEDNESS: single
       (D) TOPOLOGY: linear (ii) MOLECULE TYPE: DNA (genomic)

(ix) FEATURE:
    (A) NAME/KEY: CDS
    (B) LOCATION: 146..2873

(xi) SEQUENCE DESCRIPTION: SEQ ID NO:1:

```
ATCGATGATA CGTCGCTGTA ACACGACAAA TAGCGTGCGT TGCAGCGGTT CTGGATGGCG         60

TTATTCGTAC TTTTGCTGCG CCCATTCTTC CCTGTTCCAT CGCGGTGCGG GCATGGCGGG        120

CGTCTGCTCT CCACCTGGCA TCCAA TGA ACA TGT CTC TGT CAC GCA TTG TCA          172
                             *   Thr Cys Leu Cys His Ala Leu Ser
                             1                   5

AGG CGG CGC CCC TGC GCC GCA CCA CGC TGG CCA TGG CGC TGG GCG CGC          220
Arg Arg Arg Pro Cys Ala Ala Pro Arg Trp Pro Trp Arg Trp Ala Arg
 10              15                  20                  25

TGG GCG CCG CCC CGG CGG CGC ATG CCG ACT GGA ACA ACC AGT CCA TCG          268
Trp Ala Pro Pro Arg Arg Arg Met Pro Thr Gly Thr Thr Ser Pro Ser
                 30                  35                  40

TCA AGA CCG GTG AGC GCC AGC ATG GCA TCC ATA TCC AGG GCT CCG ACC          316
Ser Arg Pro Val Ser Ala Ser Met Ala Ser Ile Ser Arg Ala Pro Thr
                 45                  50                  55

CGG GCG GCG TAC GGA CCG CCA GCG GAA CCA CCA TCA AGG TAA GCG GCC          364
Arg Ala Ala Tyr Gly Pro Pro Ala Glu Pro Pro Ser Arg  *  Ala Ala
             60                  65                  70

GTC AGG CCC AGG GCA TCC TGC TAG AAA ATC CCG CGG CCG AGC TGC AGT          412
Val Arg Pro Arg Ala Ser Cys  *  Lys Ile Pro Arg Pro Ser Cys Ser
         75                  80                  85

TCC GGA ACG GCA GTG TCA CGT CGT CGG GAC AGT TGT CCG ACG ATG GCA          460
Ser Gly Thr Ala Val Ser Arg Arg Arg Asp Ser Cys Pro Thr Met Ala
 90                  95                 100                 105

TCC GGC GCT TTC TGG GCA CCG TCA CCG TCA AGG CCG GCA AGC TGG TCG          508
Ser Gly Ala Phe Trp Ala Pro Ser Pro Ser Arg Pro Ala Ser Trp Ser
                110                 115                 120

CCG ATC ACG CCA CGC TGG CCA ACG TTG GCG ACA CCT GGG ACG ACG ACG          556
Pro Ile Thr Pro Arg Trp Pro Thr Leu Ala Thr Pro Gly Thr Thr Thr
                125                 130                 135

GCA TCG CGC TCT ATG TGG CCG GCG AAC AGG CCC AGG CCA GCA TCG CCG          604
Ala Ser Arg Ser Met Trp Pro Ala Asn Arg Pro Arg Pro Ala Ser Pro
        140                 145                 150

ACA GCA CCC TGC AGG GCG CTG GCG GCG TGC AGA TCG AGC GCG GCG CCA          652
Thr Ala Pro Cys Arg Ala Leu Ala Ala Cys Arg Ser Ser Ala Ala Pro
    155                 160                 165

ATG TCA CGG TCC AAC GCA GCG CCA TCG TCG ACG GGG GCT TGC ATA TCG          700
Met Ser Arg Ser Asn Ala Ala Pro Ser Ser Thr Gly Ala Cys Ile Ser
170                 175                 180                 185

GCG CCC TGC AGT CAT TGC AGC CGG AAG ACC TTC CGC CCA GCC GGG TGG          748
Ala Pro Cys Ser His Cys Ser Arg Lys Thr Phe Arg Pro Ala Gly Trp
                190                 195                 200

TGC TGC GCG ACA CCA ACG TGA CCG CCG TGC CCG CCA GCG GCG CGC CCG          796
Cys Cys Ala Thr Pro Thr  *  Pro Pro Cys Pro Pro Ala Ala Arg Pro
            205                 210                 215

CGG CGG TGT CTG TGT TGG GGG CCA GTG AGC TTA CGC TCG ACG GCG GGC          844
Arg Arg Cys Leu Cys Trp Gly Pro Val Ser Leu Arg Ser Thr Ala Gly
        220                 225                 230

ACA TCA CCG GCG GGC GGG CAG CGG GGG TGG CGG CCA TGC AAG GGG CGG          892
Thr Ser Pro Ala Gly Gly Gln Arg Gly Trp Arg Pro Cys Lys Gly Arg
    235                 240                 245

TCG TGC ATC TGC AGC GCG CGA CGA TAC GGC GCG GGA CGC GCT TGC CG           940
Ser Cys Ile Cys Ser Ala Arg Arg Tyr Gly Ala Gly Thr Arg Leu Pro
250                 255                 260                 265
```

```
GCG GTG CGG TTC CCG GCG GTG CGG TTC CCG GTG GTG CGG TTC CCG GCG        988
Ala Val Arg Phe Pro Ala Val Arg Phe Pro Val Val Arg Phe Pro Ala
            270                 275                 280

GCT TCG GTC CCG GCG GCT TCG GTC CCG TCC TCG ACG GCT GGT ATG GCG       1036
Ala Ser Val Pro Ala Ala Ser Val Pro Ser Ser Thr Ala Gly Met Ala
                285                 290                 295

TGG ACG TAT CGG GCT CCA GCG TGG AGC TGG CCC AGT CGA TCG TCG AGG       1084
Trp Thr Tyr Arg Ala Pro Ala Trp Ser Trp Pro Ser Arg Ser Ser Arg
            300                 305                 310

CGC CGG AGC TGG GCG CCG CAA TCC GGG TGG GCC GCG GCG CCA GGG TGA       1132
Arg Arg Ser Trp Ala Pro Gln Ser Gly Trp Ala Ala Ala Pro Gly  *
        315                 320                 325

CGG TGC CGG GCG GCA GCT TGT CCG CAC CGC ACG GCA ATG TCA TCG AGA       1180
Arg Cys Arg Ala Ala Ala Cys Pro His Arg Thr Ala Met Ser Ser Arg
330                 335                 340                 345

CCG GCG GCG CGC GTC GCT TTG CGC CTC AAG CCG CGC CCC TGT CGA TCA       1228
Pro Ala Ala Arg Val Ala Leu Arg Leu Lys Pro Arg Pro Cys Arg Ser
                350                 355                 360

CCT TGC AGG CCG GCG CGC ATG CCC AGG GGA AAG CGC TGC TGT ACC GGG       1276
Pro Cys Arg Pro Ala Arg Met Pro Arg Gly Lys Arg Cys Cys Thr Gly
            365                 370                 375

TCC TGC CGG AGC CCG TGA AGC TGA CGC TGA CCG GGG GCG CCG ATG CGC       1324
Ser Cys Arg Ser Pro  *  Ser  *  Arg  *  Pro Gly Ala Pro Met Arg
        380                 385                 390

AGG GCG ACA TCG TCG CGA CGG AGC TGC CCT CCA TTC CCG GCA CGT CGA       1372
Arg Ala Thr Ser Ser Arg Arg Ser Cys Pro Pro Phe Pro Ala Arg Arg
395                 400                 405

TCG GGC CGC TCG ACG TGG CGC TGG CCA GCC AGG CCC GAT GGA CGG GCG       1420
Ser Gly Arg Ser Thr Trp Arg Trp Pro Ala Arg Pro Asp Gly Arg Ala
410                 415                 420                 425

CTA CCC GCG CGG TCG ACT CGC TGT CCA TCG ACA ACG CCA CCT GGG TCA       1468
Leu Pro Ala Arg Ser Thr Arg Cys Pro Ser Thr Thr Pro Pro Gly Ser
            430                 435                 440

TGA CGG ACA ACT CGA ACG TCG GTG CGC TAC GGC TGG CCA GCG ACG GCA       1516
 *  Arg Thr Thr Arg Thr Ser Val Arg Tyr Gly Trp Pro Ala Thr Ala
        445                 450                 455

GCG TCG ATT TCC AGC AGC CGG CCG AAG CTG GGC GGT TCA AGG TCC TGA       1564
Ala Ser Ile Ser Ser Ser Arg Pro Lys Leu Gly Gly Ser Arg Ser  *
            460                 465                 470

CGG TCA ATA CGC TGG CGG GTT CGG GGC TGT TCC GCA TGA ATG TCT TCG       1612
Arg Ser Ile Arg Trp Arg Val Arg Gly Cys Ser Ala  *  Met Ser Ser
475                 480                 485

CGG ACC TGG GGC TGA GCG ACA AGC TGG TCG TCA TGC AGG ACG CCA GCG       1660
Arg Thr Trp Gly  *  Ala Thr Ser Trp Ser Ser Cys Arg Thr Pro Ala
490                 495                 500                 505

GCC AGC ACA GGC TGT GGG TCC GCA ACA GCG GCA GCG AGC CGG CCA GCG       1708
Ala Ser Thr Gly Cys Gly Ser Ala Thr Ala Ala Ala Ser Arg Pro Ala
            510                 515                 520

CCA ACA CCC TGC TGC TGG TGC AGA CGC CAC TAG GCA GCG CGG CGA CCT       1756
Pro Thr Pro Cys Cys Trp Cys Arg Arg His  *  Ala Ala Arg Arg Pro
            525                 530                 535

TTA CCC TTG CCA ACA AGG ACG GCA AGG TCG ATA TCG TAC CTA TCG CT        1804
Leu Pro Leu Pro Thr Arg Thr Ala Arg Ser Ile Ser Val Pro Ile Ala
            540                 545                 550

ATC GAT TGG CCG CCA ACG GCA ATG GGC AGT GGA GCC TGG TGG GCG CGA       1852
Ile Asp Trp Pro Pro Thr Ala Met Gly Ser Gly Ala Trp Trp Ala Arg
555                 560                 565

AGG CGC CGC CGG CGC CCA AGC CCG CGC AGC CGG GTC CCC AGC CGC           1900
Arg Arg Arg Arg Arg Pro Ser Pro Arg Ser Arg Val Pro Ser Arg
570                 575                 580                 585
```

```
                                                      -continued

CGC AGC CGC CGC AGC CGC AGC CGG AAG CGC CGG CGC CGC AAC CGC CGG    1948
Arg Ser Arg Arg Ser Arg Ser Arg Lys Arg Arg Arg Arg Asn Arg Arg
                590                 595                 600

CGG GCA GGG AGT TGT CCG CCG CCG CCA ACG CGG CGG TCA ACA CGG GTG    1996
Arg Ala Gly Ser Cys Pro Pro Pro Pro Thr Arg Arg Ser Thr Arg Val
                605                 610                 615

GGG TGG GCC TGG CCA GCA CGC TCT GGT ACG CCG AAA GCA ATG CGT TGT    2044
Gly Trp Ala Trp Pro Ala Arg Ser Gly Thr Pro Lys Ala Met Arg Cys
                620                 625                 630

CCA AGC GCC TGG GCG AGT TGC GCC TGA ATC CGG ACG CCG GCG GCG CCT    2092
Pro Ser Ala Trp Ala Ser Cys Ala  *  Ile Arg Thr Pro Ala Ala Pro
                635                 640                 645

GGG GCC GCG GCT TCG CGC AAC GCC AGC AGC TGG ACA ACC GCG CCG GGC    2140
Gly Ala Ala Ala Ser Arg Asn Ala Ser Ser Trp Thr Thr Ala Pro Gly
650                 655                 660                 665

GGC GCT TCG ACC AGA AGG TGG CCG GCT TCG AGC TGG GCG CCG ACC ACG    2188
Gly Ala Ser Thr Arg Arg Trp Pro Ala Ser Ser Trp Ala Pro Thr Thr
                670                 675                 680

CGG TGG CGG TGG CCG GCG GAC GCT GGC ACC TGG GCG GGC TGG CCG GCT    2236
Arg Trp Arg Trp Pro Ala Asp Ala Gly Thr Trp Ala Gly Trp Pro Ala
                685                 690                 695

AAC GCG CGG CGA CCG CGG CTT CAC CGG CGA CGG CGG CGG CCA CAC CGA    2284
Asn Ala Arg Arg Pro Arg Leu His Arg Arg Arg Arg Arg Pro His Arg
                700                 705                 710

CAG CGT GCA TGT CGG GGG CTA TGC CAC ATA TAT CGC CGA CAG CGG TTT    2332
Gln Arg Ala Cys Arg Gly Leu Cys His Ile Tyr Arg Arg Gln Arg Phe
    715                 720                 725

CTA CCT GGA CGC GAC GCT GCG CGC CAG CCG CCT GGA GAA TGA CTT CAA    2380
Leu Pro Gly Arg Asp Ala Ala Arg Gln Pro Pro Gly Glu  *  Leu Gln
730                 735                 740                 745

GGT GGC GGG CAG CGA CGG GTA CGC GGT CAA GGG CAA GTA CCG CAC CCA    2428
Gly Gly Gly Gln Arg Arg Val Arg Gly Gln Gly Gln Val Pro His Pro
                750                 755                 760

TGG GGT GGG CGC CTC GCT CGA GGC GGG CCG GCG CTT TAC CCA TGC CGA    2476
Trp Gly Gly Arg Leu Ala Arg Gly Gly Pro Ala Leu Tyr Pro Cys Arg
                765                 770                 775

CGG CTG GTT CCT CGA GCC GCA GGC CGA GCT GGC GGT ATT CCG GGC CGG    2524
Arg Leu Val Pro Arg Ala Ala Gly Arg Ala Gly Gly Ile Pro Gly Arg
                780                 785                 790

CGG CGG TGC GTA CCG CGC GGC CAA CGG CCT GCG GGT GCG CGA CGA AGG    2572
Arg Arg Cys Val Pro Arg Gly Gln Arg Pro Ala Gly Ala Arg Arg Arg
    795                 800                 805

CGG CAG CTC GGT GCT GGG TCG CCT GGG CCT GGA GGT CGG CAA GCG CAT    2620
Arg Gln Leu Gly Ala Gly Ser Pro Gly Pro Gly Gly Arg Gln Ala His
810                 815                 820                 825

CGA ACT GGC AGG CGG CAG GCA GGT GCA GCC ATA CAT CAA GGC CAG CGT    2668
Arg Thr Gly Arg Arg Gln Ala Gly Ala Ala Ile His Gln Gly Gln Arg
                830                 835                 840

GCT GCA GGA GTT CGA CGG CGC GGG TAC GGT ACA CAC CAA CGG CAT CGC    2716
Ala Ala Gly Val Arg Arg Gly Tyr Gly Thr His Gln Arg His Arg
                845                 850                 855

GCA CCG CAC CGA ACT GCG CGG CAC GCG CGC CGA ACT GGG CCT GGG CAT    2764
Ala Pro His Arg Thr Ala Arg His Ala Arg Arg Thr Gly Pro Gly His
            860                 865                 870

GGC CGC CGC GCT GGG CCG CGG CCA CAG CCT GTA TGC CTC GTA CGA GTA    2812
Gly Arg Arg Ala Gly Pro Arg Pro Gln Pro Val Cys Leu Val Arg Val
                875                 880                 885

CTC CAA GGG CCC GAA GCT GGC CAT GCC GTG GAC CTT CCA CGC GGG CTA    2860
Leu Gln Gly Pro Glu Ala Gly His Ala Val Asp Leu Pro Arg Gly Leu
```

```
                890             895             900             905
CCG GTA CAG CTG G TAAAGCGAGG AGGGTCTATC CCCCGCGGAG GAGTTTTTCC        2913
Pro Val Gln Leu

TGGAGCTTGG CCGGTGCCAG TCTCCAGGCT CAGGCGGCCA GGGCCTGCGG GCCGGGCAGG   2973

CCGCGCTGGT GCTGGCCGAA CCATTG                                        2999
```

(2) INFORMATION FOR SEQ ID NO:2:

(i) SEQUENCE CHARACTERISTICS:
        (A) LENGTH: 3001 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 146..2876

(xi) SEQUENCE DESCRIPTION: SEQ ID NO:2:

```
ATCGATGATG CGTCGCTGTA ACACGGCAAA TACCGTGCAT TGCAGCGGTT CTGGATGGCG    60

TTCTTCGTAC GTTTGCTGCG CCCATTCTTC CCTGTTCCAT CGCGGTGCGG CCATGGCGGG   120

CGTCTGCTCT TCACCCGGCA TCCAA TGA ACA TGT CTC TGT CAC GCA TTG TCT     172
                             *   Thr Cys Leu Cys His Ala Leu Ser
                             1                 5

TGG CGG CGC CCC TGC GCC GCA CCA CAC TGG CCA TGG CGC TGG GCG CGC     220
Trp Arg Arg Pro Cys Ala Ala Pro His Trp Pro Trp Arg Trp Ala Arg
 10              15                  20                  25

TGG GCG CCG CGC CCG CCG CGT ACG CCG ACT GGA ACA ACC AGT CCA TCA     268
Trp Ala Pro Arg Pro Pro Arg Thr Pro Thr Gly Thr Thr Ser Pro Ser
             30                  35                  40

TCA AGG CCG GCG AGC GCC AGC ACG GCA TCC ACA TCA AGC AAA GCG ATG     316
Ser Arg Pro Ala Ser Ala Ser Thr Ala Ser Thr Ser Ser Lys Ala Met
             45                  50                  55

GCG CCG GCG TAC GGA CCG CCA CCG GAA CGA CCA TCA AGG TAA GCG GTC     364
Ala Pro Ala Tyr Gly Pro Pro Pro Glu Arg Pro Ser Arg  *  Ala Val
             60                  65                  70

GTC AGG CCC AGG GCG TCC TGC TGG AAA ATC CCG CGG CCG AGC TGC GGT     412
Val Arg Pro Arg Ala Ser Cys Trp Lys Ile Pro Arg Pro Ser Cys Gly
 75              80                  85

TCC AGA ACG GCA GCG TCA CGT CTT CGG GAC AGC TGT TCG ACG AAG GCG     460
Ser Arg Thr Ala Ala Ser Arg Leu Arg Asp Ser Cys Ser Thr Lys Ala
 90                  95                 100                 105

TCC GGC GCT TTC TGG GCA CCG TCA CCG TCA AGG CCG GCA AGC TGG TCG     508
Ser Gly Ala Phe Trp Ala Pro Ser Pro Ser Arg Pro Ala Ser Trp Ser
                 110                 115                 120

CCG ATC ACG CCA CGC TGG CCA ACG TCA GCG ACA CCC GGG ACG ACG ACG     556
Pro Ile Thr Pro Arg Trp Pro Thr Ser Ala Thr Pro Gly Thr Thr Thr
             125                 130                 135

GCA TCG CGC TCT ATG TGG CCG GCG AGC AGG CCC AGG CCA GCA TCG CCG     604
Ala Ser Arg Ser Met Trp Pro Ala Ser Arg Pro Arg Pro Ala Ser Pro
             140                 145                 150

ACA GCA CCC TGC AGG GCG CGG GCG GCG TGC GGG TCG AGC GCG GCG CCA     652
Thr Ala Pro Cys Arg Ala Arg Ala Ala Cys Gly Ser Ser Ala Ala Pro
             155                 160                 165

ATG TCA CGG TCC AAC GCA GCA CCA TCG TTG ACG GGG GCT GCA TA TCG      700
Met Ser Arg Ser Asn Ala Ala Pro Ser Leu Thr Gly Ala Cys Ile Ser
170                 175                 180                 185

GCA CCC TGC AGC CGC TGC AGC CGG AAG ACC TTC CGC CCA GCC GGG TGG     748
```

```
Ala Pro Cys Ser Arg Cys Ser Arg Lys Thr Phe Arg Pro Ala Gly Trp
            190                 195                 200

TGC TGG GCG ACA CCA GCG TGA CCG CCG TGC CCG CCA GCG GCG CGC CCG        796
Cys Trp Ala Thr Pro Ala  *  Pro Pro Cys Pro Pro Ala Ala Arg Pro
            205                 210                 215

CGG CGG TGT CTG TAT TCG GGG CCA ATG AGC TTA CGG TTG ATG GCG GGC        844
Arg Arg Cys Leu Tyr Ser Gly Pro Met Ser Leu Arg Leu Met Ala Gly
            220                 225                 230

ACA TCA CCG GGG GGC GGG CAG CGG GGG TGG CGG CCA TGG ACG GGG CGA        892
Thr Ser Pro Gly Gly Gly Gln Arg Gly Trp Arg Pro Trp Thr Gly Arg
            235                 240                 245

TCG TGC ATC TGC AGC GCG CGA CGA TAC GGC GGG GGG ACG CGC CTG CCG        940
Ser Cys Ile Cys Ser Ala Arg Arg Tyr Gly Gly Gly Thr Arg Leu Pro
250                 255                 260                 265

GCG GTG CGG TTC CAG GCG GTG CTG TTC CCG GCG GCT TCG GCC CCC TCC        988
Ala Val Arg Phe Gln Ala Val Leu Phe Pro Ala Ala Ser Ala Pro Ser
            270                 275                 280

TTG ACG GCT GGT ATG GCG TGG ATG TAT CGG ATT CCA CCG TGG ACC TCG       1036
Leu Thr Ala Gly Met Ala Trp Met Tyr Arg Ile Pro Pro Trp Thr Ser
            285                 290                 295

CTC AGT CGA TCG TCG AGG CGC CGC AGC TGG GCG CCG CGA TCC GGG CGG       1084
Leu Ser Arg Ser Ser Arg Arg Arg Ser Trp Ala Pro Arg Ser Gly Arg
            300                 305                 310

GCC GCG GCG CCA GGG TGA CGG TGT CGG GCG GCA GCT TGT CCG CAC CGC       1132
Ala Ala Ala Pro Gly  *  Arg Cys Arg Ala Ala Ala Cys Pro His Arg
            315                 320                 325

ACG GCA ATG TCA TCG AGA CCG GCG GCG GCG CGC GTC GCT TCC CGC CTC       1180
Thr Ala Met Ser Ser Arg Pro Ala Ala Ala Arg Val Ala Ser Arg Leu
330                 335                 340                 345

CGG CCT CGC CCC TGT CGA TCA CCT TGC AGG CGG GCG CAC GGG CGC AGG       1228
Arg Pro Arg Pro Cys Arg Ser Pro Cys Arg Arg Ala His Gly Arg Arg
            350                 355                 360

GGA GGG CGC TGC TGT ACC GGG TCC TGC CGG AGC CCG TGA AGC TGA CGC       1276
Gly Gly Arg Cys Cys Thr Gly Ser Cys Arg Ser Pro  *  Ser  *  Arg
            365                 370                 375

TGG CGG GCG GCG CCC AGG GGC AGG GCG ACA TCG TCG CGA CGG AGC TGC       1324
Trp Arg Ala Ala Pro Arg Gly Arg Ala Thr Ser Ser Arg Arg Ser Cys
            380                 385                 390

CTC CCA TTC CAG GCG CGT CGA GCG GGC CGC TCG ACG TGG CGC TGG CCA       1372
Leu Pro Phe Gln Ala Arg Arg Ala Gly Arg Ser Thr Trp Arg Trp Pro
            395                 400                 405

GCC AGG CCC GAT GGA CGG GCG CTA CCC GCG CGG TCG ACT CGC TGT CCA       1420
Ala Arg Pro Asp Gly Arg Ala Leu Pro Ala Arg Ser Thr Arg Cys Pro
410                 415                 420                 425

TCG ACA ACG CCA CCT GGG TCA TGA CGG ACA ACT CGA ACG TCG GCG CGC       1468
Ser Thr Thr Pro Pro Gly Ser  *  Arg Thr Thr Arg Thr Ser Ala Arg
            430                 435                 440

TGC GGC TGG CCA GCG ACG GCA GCG TCG ATT CCA GCA GCC GGC CGA AG        1516
Cys Gly Trp Pro Ala Thr Ala Ala Ser Ile Ser Ser Ser Arg Pro Lys
            445                 450                 455

CTG GGC GGT TCA AGT GCC TGA TGG TCG ATA CGC TGG CGG GTT CGG GGC       1564
Leu Gly Gly Ser Ser Ala  *  Trp Ser Ile Arg Trp Arg Val Arg Gly
            460                 465                 470

TGT TCC GCA TGA ATG TCT TCG CGG ACC TGG GGC TGA GCG ACA AGC TGG       1612
Cys Ser Ala  *  Met Ser Ser Arg Thr Trp Gly  *  Ala Thr Ser Trp
            475                 480                 485

TCG TCA TGC GGG ACG CCA GCG GCC AGC ACA GGC TGT TGG TCC GCA ACA       1660
Ser Ser Cys Gly Thr Pro Ala Ala Ser Thr Gly Cys Trp Ser Ala Thr
490                 495                 500                 505
```

```
GCG GCA GCC GAG CCG GCC AGC GGC AAC ACC ATG CTG CTG GTG CAG ACG      1708
Ala Ala Ala Glu Pro Ala Ser Gly Asn Thr Met Leu Leu Val Gln Thr
            510                 515                 520

CCA CGA GGC AGC GCG GCG ACC TTT ACC CTT GCC AAC AAG GAC GGC AAG      1756
Pro Arg Gly Ser Ala Ala Thr Phe Thr Leu Ala Asn Lys Asp Gly Lys
            525                 530                 535

GTC GAT ATC GGT ACC TAC CGC TAT CGA TTG GCC GCC AAC GGC AAT GGG      1804
Val Asp Ile Gly Thr Tyr Arg Tyr Arg Leu Ala Ala Asn Gly Asn Gly
            540                 545                 550

CAG TGG AGC CTG GTG GGC GCG AAG GCG CCG CCG GCG CCC AAG CCC GCG      1852
Gln Trp Ser Leu Val Gly Ala Lys Ala Pro Pro Ala Pro Lys Pro Ala
            555                 560                 565

CCG CAG CCC GGT CCC CAG CCC GGT CCC CAG CCG CCG CAG CCG CCG CAG      1900
Pro Gln Pro Gly Pro Gln Pro Gly Pro Gln Pro Pro Gln Pro Pro Gln
570                 575                 580                 585

CCG CCG CAG CCG CCA CAG AGG CAG CCG GAA GCG CCG GCG CCG CAA CCG      1948
Pro Pro Gln Pro Pro Gln Arg Gln Pro Glu Ala Pro Ala Pro Gln Pro
                590                 595                 600

CCG GCG GGC AGG GAG TTG TCC GCC GCC GCC AAC GCG GCG GTC AAC ACG      1996
Pro Ala Gly Arg Glu Leu Ser Ala Ala Ala Asn Ala Ala Val Asn Thr
            605                 610                 615

GGT GGG GTG GGC CTG GCC AGC ACG CTC TGG TAC GCC GAA AGC AAT GCG      2044
Gly Gly Val Gly Leu Ala Ser Thr Leu Trp Tyr Ala Glu Ser Asn Ala
            620                 625                 630

TTG TCC AAG CGC CTG GGC GAG TTG CGC CTG AAT CCG GAC GCC GGC GGC      2092
Leu Ser Lys Arg Leu Gly Glu Leu Arg Leu Asn Pro Asp Ala Gly Gly
            635                 640                 645

GCT TGG GGC CGC GGC TTC GCG CAA CGC CAG CAA CTG GAC AAC CGC GCC      2140
Ala Trp Gly Arg Gly Phe Ala Gln Arg Gln Gln Leu Asp Asn Arg Ala
650                 655                 660                 665

GGG CGG CGC TTC GAC CAG AAG GTG GCC GGC TTC GAG CTG GGC GCC GAC      2188
Gly Arg Arg Phe Asp Gln Lys Val Ala Gly Phe Glu Leu Gly Ala Asp
            670                 675                 680

CAC GCG GTG GCG GTG GCC GGC GGG CGC TGG CAC CTG GGC GGG CTG GCC      2236
His Ala Val Ala Val Ala Gly Gly Arg Trp His Leu Gly Gly Leu Ala
            685                 690                 695

GGC TAT ACG CGC GGC GAC CGC GGC TTT ACC GGC GAC GGC GGC GGC CAC      2284
Gly Tyr Thr Arg Gly Asp Arg Gly Phe Thr Gly Asp Gly Gly Gly His
            700                 705                 710

ACC GAC AGC GTG CAT GTC GGG GGC TAT GCC ACC TAT ATC GCC AAC AGC      2332
Thr Asp Ser Val His Val Gly Gly Tyr Ala Thr Tyr Ile Ala Asn Ser
            715                 720                 725

GGT TTC TAC CTG GAC GCG ACG CTG CGC GCC AGC CGC CTC GAA AAT GAC      2380
Gly Phe Tyr Leu Asp Ala Thr Leu Arg Ala Ser Arg Leu Glu Asn Asp
730                 735                 740                 745

TTC AAG GTG GCG GGC AGC GAT GGG TAC GCG GTC AAG GGC AAG TAC CGC      2428
Phe Lys Val Ala Gly Ser Asp Gly Tyr Ala Val Lys Gly Lys Tyr Arg
            750                 755                 760

ACC CAT GGG GTA GGC GCC TCG CTC GAG GCG GGC CGG CGC TTC GCC CAT      2476
Thr His Gly Val Gly Ala Ser Leu Glu Ala Gly Arg Arg Phe Ala His
            765                 770                 775

GCC GAC GGC TGG TTC CTC GAG CCG CAG GCC GAG CTG GCG GTG TTC CGG      2524
Ala Asp Gly Trp Phe Leu Glu Pro Gln Ala Glu Leu Ala Val Phe Arg
            780                 785                 790

GTC GGC GGC GGT TCG TAC CGC GCG GCC AAT GGC CTG CGG GTG CGC GAC      2572
Val Gly Gly Gly Ser Tyr Arg Ala Ala Asn Gly Leu Arg Val Arg Asp
            795                 800                 805

GAA GGC GGC AGC TCG GTG CTG GGT CGC CTG GGC CTG GAG GTC GGC AAG      2620
Glu Gly Gly Ser Ser Val Leu Gly Arg Leu Gly Leu Glu Val Gly Lys
810                 815                 820                 825
```

```
CGC ATC GAA CTG GCA GGC GGC AGG CAG GTG CAG CCA TAC ATC AAG GCC     2668
Arg Ile Glu Leu Ala Gly Gly Arg Gln Val Gln Pro Tyr Ile Lys Ala
                    830                 835                 840

AGC GTG CTG CAG GAG TTC GAC GGC GCG GGT ACG GTA CGC ACC AAC GGC     2716
Ser Val Leu Gln Glu Phe Asp Gly Ala Gly Thr Val Arg Thr Asn Gly
                845                 850                 855

ATC GCG CAC CGC ACC GAA CTG CGC GGC ACG CGC GCC GAA CTG GGC CTG     2764
Ile Ala His Arg Thr Glu Leu Arg Gly Thr Arg Ala Glu Leu Gly Leu
            860                 865                 870

GGC ATG GCC GCC GCG CTG GGC CGC GGC CAC AGC CTG TAT GCC TCG TAC     2812
Gly Met Ala Ala Ala Leu Gly Arg Gly His Ser Leu Tyr Ala Ser Tyr
        875                 880                 885

GAG TAC TCC AAG GGG CCG AAG CTG GCC ATG CCG TGG ACC TTC CAC GCG     2860
Glu Tyr Ser Lys Gly Pro Lys Leu Ala Met Pro Trp Thr Phe His Ala
890                 895                 900                 905

GGC TAC CGG TAC AGC T GGTAAAGCGA AAGGGTCCA TCCCCCCGCG GGGAGATTT     2916
Gly Tyr Arg Tyr Ser
                910

TCCTGGAGGT TGGCCGGTGC CAGTCTCCAG GCTCAGGCGG CCAGGGCGTG CGGGCCGGGC    2976

AGGCCGTGCT GGTGCTGGCC GAACC                                         3001

(2) INFORMATION FOR SEQ ID NO:3:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 146..2906

(xi) SEQUENCE DESCRIPTION: SEQ ID NO:3:

ATCGATGATG CGTCGCTGTA ACACGGCAAA TACCGTGCAT TGCAGCGGTT CTGGATGGCG     60

TTCTTCGTAC GTTTGCTGCG CCCATTCTTC CCTGTTCCAT CGCGGTGCGG GCATGGCGGG    120

CGTCTGCTCT TCACCCGGCA TCCAA TGA ACA TGT CTC TGT CAC GCA TTG TCA      172
                              *  Thr Cys Leu Cys His Ala Leu Ser
                              1                  5

AGG CGG CGC CCC TGC GCC GCA CCA CAC TGG CCA TGG CGC TGG GCG CGC      220
Arg Arg Arg Pro Cys Ala Ala Pro His Trp Pro Trp Arg Trp Ala Arg
 10              15                  20                  25

TGG GCG CCG CGC CCG CCG CGT ACG CCG ACT GGA ACA ACC AGT CCA TCA      268
Trp Ala Pro Arg Pro Pro Arg Thr Pro Thr Gly Thr Thr Ser Pro Ser
                 30                  35                  40

TCA AGG CCG GCG AGC GCC AGC ACG GCA TCC ACA TCA AGC AAA GCG ATG      316
Ser Arg Pro Ala Ser Ala Ser Thr Ala Ser Thr Ser Ser Lys Ala Met
             45                  50                  55

GCG CCG GCG TAC GGA CCG CCA CCG GAA CGA CCA TCA AGG TAA GCG GTC      364
Ala Pro Ala Tyr Gly Pro Pro Pro Glu Arg Pro Ser Arg  *  Ala Val
             60                  65                  70

GTC AGG CCC AGG GCG TCC TGC TGG AAA ATC CCG CGG CCG AGC TGC GGT      412
Val Arg Pro Arg Ala Ser Cys Trp Lys Ile Pro Arg Pro Ser Cys Gly
 75                  80                  85

TCC AGA ACG GCA GCG TCA CGT CTT CGG GAC AGC TGT TCG ACG AAG GCG      460
Ser Arg Thr Ala Ala Ser Arg Leu Arg Asp Ser Cys Ser Thr Lys Ala
 90                  95                 100                 105

TCC GGC GCT TTC TGG GCA CCG TCA CCG TCA AGG CCG GCA AGC TGG TCG      508
```

```
Ser Gly Ala Phe Trp Ala Pro Ser Pro Ser Arg Pro Ala Ser Trp Ser
            110                 115                 120

CCG ATC ACG CCA CGC TGG CCA ACG TCA GCG ACA CCC GGG ACG ACG ACG      556
Pro Ile Thr Pro Arg Trp Pro Thr Ser Ala Thr Pro Gly Thr Thr Thr
        125                 130                 135

GCA TCG CGC TCT ATG TGG CCG GCG AGC AGG CCC AGG CCA GCA TCG CCG      604
Ala Ser Arg Ser Met Trp Pro Ala Ser Arg Pro Arg Pro Ala Ser Pro
            140                 145                 150

ACA GCA CCC TGC AGG GCG CGG GCG GCG TGC GGG TCG AGC GCG GCG CCA      652
Thr Ala Pro Cys Arg Ala Arg Ala Ala Cys Gly Ser Ser Ala Ala Pro
        155                 160                 165

ATG TCA CGG TCC AAC GCA GCA CCA TCG TTG ACG GGG GCT TGC ATA TCG      700
Met Ser Arg Ser Asn Ala Ala Pro Ser Leu Thr Gly Ala Cys Ile Ser
170                 175                 180                 185

GCA CCC TGC AGC CGC TGC AGC CGG AAG ACC TTC CGC CCA GCC GGG TGG      748
Ala Pro Cys Ser Arg Cys Ser Arg Lys Thr Phe Arg Pro Ala Gly Trp
            190                 195                 200

TGC TGG GCG ACA CCA GCG TGA CCG CCG TGC CCG CCA GCG GCG CGC CCG      796
Cys Trp Ala Thr Pro Ala  *  Pro Pro Cys Pro Pro Ala Ala Arg Pro
        205                 210                 215

CGG CGG TGT TTG TAT TCG GGG CCA ATG AGC TTA CGG TTG ATG GCG GGC      844
Arg Arg Cys Leu Tyr Ser Gly Pro Met Ser Leu Arg Leu Met Ala Gly
            220                 225                 230

ACA TCA CCG GGG GGC GGG CAG CGG GGG TGG CGG CCA TGG ACG GGG CGA      892
Thr Ser Pro Gly Gly Gly Gln Arg Gly Trp Arg Pro Trp Thr Gly Arg
        235                 240                 245

TCG TGC ATC TGC AGC GCG CGA CGA TAC GGC GGG GGG ACG CGC CTG CCG      940
Ser Cys Ile Cys Ser Ala Arg Arg Tyr Gly Gly Gly Thr Arg Leu Pro
250                 255                 260                 265

GCG GTG CGG TTC CAG GCG GTG CGG TTC CCG GCG GTG CCG TTC CCG GCG      988
Ala Val Arg Phe Gln Ala Val Arg Phe Pro Ala Val Pro Phe Pro Ala
            270                 275                 280

GCT TCG GCC CCC TCC TTG ACG GCT GGT ATG GCG TGG ATG TAT CGG ACT     1036
Ala Ser Ala Pro Ser Leu Thr Ala Gly Met Ala Trp Met Tyr Arg Thr
        285                 290                 295

CCA CCG TGG ACC TCG CTC AGT CGA TCG TCG AGG CGC CGC AGC TGG GCG     1084
Pro Pro Trp Thr Ser Leu Ser Arg Ser Ser Arg Arg Arg Ser Trp Ala
            300                 305                 310

CCG CGA TCC GGG CGG GCC GCG GCG CCA GGG TGA CGG TGT CGG GCG GCA     1132
Pro Arg Ser Gly Arg Ala Ala Ala Pro Gly  *  Arg Cys Arg Ala Ala
        315                 320                 325

GCT TGT CCG CAC CGC ACG GCA ATG TCA TCG AGA CCG GCG GCG GTG CGC     1180
Ala Cys Pro His Arg Thr Ala Met Ser Ser Arg Pro Ala Ala Val Arg
330                 335                 340                 345

GTC GCT TCC CGC CTC CGG CCT CGC CCC TGT CGA TCA CCT TGC AGG CGG     1228
Val Ala Ser Arg Leu Arg Pro Arg Pro Cys Arg Ser Pro Cys Arg Arg
            350                 355                 360

GCG CAC GGG CGC AGG GGA GGG CGC TGC TGT ACC GGG TCC TGC CGG AGC     1276
Ala His Gly Arg Arg Gly Gly Arg Cys Cys Thr Gly Ser Cys Arg Ser
        365                 370                 375

CCG TGA AGC TGA CGC TGG CGG GCG GCG CCC AGG GGC AGG GCG ACA TCG     1324
Pro  *  Ser  *  Arg Trp Arg Ala Ala Pro Arg Gly Arg Ala Thr Ser
            380                 385                 390

TCG CGA CGG AGC TGC CTC CCA TTC CAG GCG CGT CGA GCG GGC CGC TCG     1372
Ser Arg Arg Ser Cys Leu Pro Phe Gln Ala Arg Arg Ala Gly Arg Ser
        395                 400                 405

ACG TGG CGC TGG CCA GCC AGG CCC GAT GGA CGG GCG CTA CCC GCG CGG     1420
Thr Trp Arg Trp Pro Ala Arg Pro Asp Gly Arg Ala Leu Pro Ala Arg
410                 415                 420                 425
```

-continued

```
TCG ACT CGC TGT CCA TCG ACA ACG CCA CCT GGG TCA TGA CGG ACA ACT    1468
Ser Thr Arg Cys Pro Ser Thr Thr Pro Pro Gly Ser  *  Arg Thr Thr
                430                 435                 440

CGA ACG TCG GCG CGC TGC GGC TGG CCA GCG ACG GCA GCG TCG ATT TCC    1516
Arg Thr Ser Ala Arg Cys Gly Trp Pro Ala Thr Ala Ala Ser Ile Ser
                445                 450                 455

AGC AGC CGG CCG AAG CTG GGC GGT TCA AGG TCC TGA TGG TCG ATA CGC    1564
Ser Ser Arg Pro Lys Leu Gly Gly Ser Arg Ser  *  Trp Ser Ile Arg
                460                 465                 470

TGG CGG GTT CGG GGC TGT TCC GCA TGA ATG TCT TCG CGG ACC TGG GGC    1612
Trp Arg Val Arg Gly Cys Ser Ala  *  Met Ser Ser Arg Thr Trp Gly
                475                 480                 485

TGA GCG ACA AGC TGG TCG TCA TGC GGG ACG CCA GCG GCC AGC ACA GGC    1660
 *  Ala Thr Ser Trp Ser Ser Cys Gly Thr Pro Ala Ala Ser Thr Gly
490                 495                 500                 505

TGT GGG TCC GCA ACA GCG GCA GCG AGC CGG CCA GCG GCA ACA CCA TGC    1708
Cys Gly Ser Ala Thr Ala Ala Ala Ser Arg Pro Ala Ala Thr Pro Cys
                510                 515                 520

TGC TGG TGC AGA CGC CAC GAG GCA GCG CGG CGA CCT TTA CCC TTG CCA    1756
Cys Trp Cys Arg Arg His Glu Ala Ala Arg Arg Pro Leu Pro Leu Pro
                525                 530                 535

ACA AGG ACG GCA AGG TCG ATA TCG GTA CCT ACC GCT ATC GAT TGG CCG    1804
Thr Arg Thr Ala Arg Ser Ile Ser Val Pro Thr Ala Ile Asp Trp Pro
                540                 545                 550

CCA ACG GCA ATG GGC AGT GGA GCC TGG TGG GCG CGA AGG CGC CGC CGG    1852
Pro Thr Ala Met Gly Ser Gly Ala Trp Trp Ala Arg Arg Arg Arg
555                 560                 565

CGC CCA AGC CCG CGC CGC AGC CCG GTC CCC AGC CCG GTC CCC AGC CGC    1900
Arg Pro Ser Pro Arg Arg Ser Pro Val Pro Ser Pro Val Pro Ser Arg
570                 575                 580                 585

CGC AGC CGC CGC AGC CGC CGC AGC CGC CGC AGC CGC CGC AGC CGC CAC    1948
Arg Ser Arg Arg Ser Arg Arg Ser Arg Arg Ser Arg Arg Ser Arg His
                590                 595                 600

AGA GGC AGC CGG AAG CGC CGG CGC CGC AAC CGC CGG CGG GCA GGG AGT    1996
Arg Gly Ser Arg Lys Arg Arg Arg Arg Asn Arg Arg Arg Ala Gly Ser
                605                 610                 615

TGT CCG CCG CCG CCA ACG CGG CGG TCA ACA CGG GTG GGG TGG GCC TGG    2044
Cys Pro Pro Pro Pro Thr Arg Arg Ser Thr Arg Val Gly Trp Ala Trp
                620                 625                 630

CCA GCA CGC TCT GGT ACG CCG AAA GCA ATG CGT TGT CCA AGC GCC TGG    2092
Pro Ala Arg Ser Gly Thr Pro Lys Ala Met Arg Cys Pro Ser Ala Trp
635                 640                 645

GCG AGT TGC GCC TGA ATC CGG ACG CCG GCG GCG CTT GGG GCC GCG GCT    2140
Ala Ser Cys Ala  *  Ile Arg Thr Pro Ala Ala Leu Gly Ala Ala Ala
650                 655                 660                 665

TCG CGC AAC GCC AGC AAC TGG ACA ACC GCG CCG GGC GGC GCT TCG ACC    2188
Ser Arg Asn Ala Ser Asn Trp Thr Thr Ala Pro Gly Gly Ala Ser Thr
                670                 675                 680

AGA AGG TGG CCG GCT TCG AGC TGG GCG CCG ACC ACG CGG TGG CGG TGG    2236
Arg Arg Trp Pro Ala Ser Ser Trp Ala Pro Thr Thr Arg Trp Arg Trp
                685                 690                 695

CCG GCG GGC GCT GGC ACC TGG GCG GGC TGG CCG GCT ATA CGC GCG GCG    2284
Pro Ala Gly Ala Gly Thr Trp Ala Gly Trp Pro Ala Ile Arg Ala Ala
                700                 705                 710

ACC GCG GCT TTA CCG GCG ACG GCG GCG GCC ACA CCG ACA GCG TGC ATG    2332
Thr Ala Ala Leu Pro Ala Thr Ala Ala Ala Thr Pro Thr Ala Cys Met
                715                 720                 725

TCG GGG GCT ATG CCA CCT ATA TCG CCA ACA GCG GTT TCT ACC TGG ACG    2380
Ser Gly Ala Met Pro Pro Ile Ser Pro Thr Ala Val Ser Thr Trp Thr
730                 735                 740                 745
```

```
CGA CGC TGC GCG CCA GCC GCC TCG AAA ATG ACT TCA AGG TGG CGG GCA      2428
Arg Arg Cys Ala Pro Ala Ala Ser Lys Met Thr Ser Arg Trp Arg Ala
                    750                 755                 760

GCG ATG GGT ACG CGG TCA AGG GCA AGT ACC GCA CCC ATG GGG TAG GCG      2476
Ala Met Gly Thr Arg Ser Arg Ala Ser Thr Ala Pro Met Gly  *  Ala
                765                 770                 775

TCT CGC TCG AGG CGG GCC GGC GCT TCG CCC ATG CCG ACG GCT GGT TCC      2524
Ser Arg Ser Arg Arg Ala Gly Ala Ser Pro Met Pro Thr Ala Gly Ser
                780                 785                 790

TCG AGC CGC AGG CCG AGC TGG CGG TGT TCC GGG TCG GCG GCG GTG CGT      2572
Ser Ser Arg Arg Pro Ser Trp Arg Cys Ser Gly Ser Ala Ala Val Arg
            795                 800                 805

ACC GCG CGG CCA ATG GCC TGC GGG TGC GCG ACG AAG GCG GCA GCT CGG      2620
Thr Ala Arg Pro Met Ala Cys Gly Cys Ala Thr Lys Ala Ala Ala Arg
810                 815                 820                 825

TGC TGG GTC GCC TGG GCC TGG AGG TCG GCA AGC GCA TCG AAC TGG CAG      2668
Cys Trp Val Ala Trp Ala Trp Arg Ser Ala Ser Ala Ser Asn Trp Gln
                830                 835                 840

GCG GCA GGC AGG TGC AGC CAT ACA TCA AGG CCA GCG TGT TGC AGG AGT      2716
Ala Ala Gly Arg Cys Ser His Thr Ser Arg Pro Ala Cys Cys Arg Ser
                845                 850                 855

TCG ACG GCG CGG GTA CGG TAC GCA CCA ACG GCA TCG CGC ATC GCA CCG      2764
Ser Thr Ala Arg Val Arg Tyr Ala Pro Thr Ala Ser Arg Ile Ala Pro
                860                 865                 870

AAC TGC GCG GCA CGC GCG CCG AAC TGG GCC TGG GCA TGG CCG CCG CGC      2812
Asn Cys Ala Ala Arg Ala Pro Asn Trp Ala Trp Ala Trp Pro Pro Arg
            875                 880                 885

TGG GCC GCG GCC ACA GCC TGT ATG CCT CGT ACG AGT ACT CCA AGG GCC      2860
Trp Ala Ala Ala Thr Ala Cys Met Pro Arg Thr Ser Thr Pro Arg Ala
890                 895                 900                 905

CGA AGC TGG CCA TGC CGT GGA CCT TCC ACG CGG GCT ACC GGT ACA G        2906
Arg Ser Trp Pro Cys Arg Gly Pro Ser Thr Arg Ala Thr Gly Thr
                910                 915                 920

CTGGTAAAGC GAGAAGGGTC CATCCCCCGC GGAGGAGTTT TTCCTGGAGG TTGGCCGGTG    2966

CCAGTCTCCA GGCTCAGGCG GCCAGGGCCT GCGG                                3000
```

(2) INFORMATION FOR SEQ ID NO:4:

(i) SEQUENCE CHARACTERISTICS:
        (A) LENGTH: 6 amino acids
        (B) TYPE: amino acid
        (C) TOPOLOGY: linear (ii) MOLECULE TYPE: peptide (xi) SEQUENCE DESCRIPTION: SEQ ID NO: 4:

```
Pro Gly Pro Gln Pro Pro
1               5
```

(2) INFORMATION FOR SEQ ID NO:5:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:5:

```
Ala Pro Gln Pro Gly Pro Gln Pro Pro Gln Pro Gln Pro Gln Pro
1               5                   10                  15
```

-continued

```
Glu Ala Pro Ala Pro Gln Pro
            20
```